United States Patent
Berthelon et al.

(10) Patent No.: US 7,323,458 B1
(45) Date of Patent: Jan. 29, 2008

(54) DIHYDROBENZODIAZEPINS AND THEIR USE FOR TREATING DYSLIPIDEMIA

(75) Inventors: Jean-Jacques Berthelon, Lyons (FR); Daniel Guerrier, Saint Genis Laval (FR); Michel Brunet, Toussieu (FR); Jean-Jacques Zeiller, Lyons (FR); Francis Contard, Lyons (FR); Fréderic Ausseil, Toulouse (FR)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 435 days.

(21) Appl. No.: 10/019,683

(22) PCT Filed: Jul. 4, 2000

(86) PCT No.: PCT/EP00/06230

§ 371 (c)(1),
(2), (4) Date: May 20, 2004

(87) PCT Pub. No.: WO01/02373

PCT Pub. Date: Jan. 11, 2001

(30) Foreign Application Priority Data

Jul. 6, 1999 (FR) .................... 99 08714

(51) Int. Cl.
*A61P 7/00* (2006.01)
*A61K 31/55* (2006.01)
*C07D 243/04* (2006.01)

(52) U.S. Cl. .................... 514/220; 540/497; 540/498

(58) Field of Classification Search ............... 514/220; 540/497, 498
See application file for complete search history.

(56) References Cited

U.S. PATENT DOCUMENTS

| 3,780,023 | A | 12/1973 | Suh et al. |
| 4,554,273 | A | 11/1985 | Bayssat et al. |
| 5,260,339 | A | 11/1993 | Martin et al. |

FOREIGN PATENT DOCUMENTS

| FR | 2540871 | | 8/1984 |
| FR | 2 550 199 | * | 2/1985 |
| HU | 182884 | | 6/1983 |
| WO | WO 9605188 | | 2/1996 |

OTHER PUBLICATIONS

Linda L. Setescak et al: "4-Aryl-4, 5-Dihydro-3H-1, 3-Benzodiazepines.3. 2-Phenyl and 2-Amino Analogues as Potential Antihypertensive Agents" Journal of Medicinal Chemistry., vol. 27, No. 3,—1984 pp. 401-404.
Timothy Jen et al.: "Amiidines. 4. Synthesis of Tricyclic Guanidines Related to 1,2,3,5-Tetrahydroimidazo(2,1-B)Quinazolin E, A New Antihypertensive Agent" Journal of Medicinal Chemistry., vol. 16, No. 4-1973 pp. 407-411.

* cited by examiner

*Primary Examiner*—Brenda Coleman
(74) *Attorney, Agent, or Firm*—Millen, White, Zelano & Branigan, P.C.

(57) ABSTRACT

The invention concerns a benzodiazepin derivative of formula (I) and their use for treating dyslipidemia, atherosclerosis, diabetes and its complications.

16 Claims, No Drawings

DIHYDROBENZODIAZEPINS AND THEIR USE FOR TREATING DYSLIPIDEMIA

This application is a national stage entry under 35 USC § 371 of PCT/EP00/06230, filed on Jul. 4, 2000, and claims priority to FR 99/08,714, filed on Jul. 6, 1999.

The present invention relates to dihydrobenzodiazepines which may be used in the treatment of dyslipidaemia, atherosclerosis and diabetes and its complications.

In most countries, cardiovascular disease remains one of the major diseases and the main cause of death. About one third of men develop a major cardiovascular disease before the age of 60, women show a lower risk (ratio 1 to 10). With advancing years (after the age of 65, women become just as vulnerable to cardiovascular diseases as men), this disease increases even more in scale. Vascular diseases such as coronary disease, strokes, restenosis and peripheral vascular disease remain the first cause of death and handicap throughout the world.

Whereas diet and lifestyle can accelerate the development of cardiovascular diseases, a genetic predisposition leading to dyslipidaemia is a significant factor in cardiovascular accidents and death. The development of atherosclerosis appears to be linked mainly to dyslipidaemia, which means abnormal levels of lipoproteins in the blood plasma. This dysfunction is particularly evident in coronary disease, diabetes and obesity.

The concept intended to explain the development of atherosclerosis has mainly been focused on the metabolism of cholesterol and on the metabolism of triglycerides.

In man, hypertriglyceridaemia is a relatively common complaint, with 10% of men between 35 and 39 years old showing plasmatic concentrations of greater than 250 mg/dl (LaRosa J. C., L. E. Chambless, M. H. Criqui, I. D. Frantz, C. J. Glueck, G. Heiss, and J. A. Morisson, 1986. Circulation 73: Suppl. 1.12-29.). In some individuals, the disruption is of genetic origin, but for others secondary causes such as excessive consumption of alcohol, obesity, diabetes or hypothyroidism predominate.

The genetic causes of hypertriglyceridaemia that have been clearly identified are homozygosity for dysfunctional alleles of LPL or of apo CII [Fojo S. S., J. L. de Gennes, U. Beisiegel, G. Baggio, S. F. Stahlenhoef, J. D. Brunzell and H. B. Brewer, Jr 1991. Adv. Exp. Med. Biol. 285: 329-333; Brunzell, J. D. 1995. In the Metabolic Basis of Inherited Disease, 6$^{th}$ ed. C. Scriver, A. Sly and D. Valle, published by McGraw-Hill, Inc., New York. 1913-1932]. However, these conditions occur in only one case in a million and are considered as rare. Tests exist, derived from studies performed on man and on mice that are deficient in LPL [Brunzell, J. D. 1995. In the Metabolic Basis of Inherited Disease, 6$^{th}$ ed. C. Scriver, A. Sly and D. Valle, published by McGraw-Hill, Inc., New York. 1913-1932; Coleman T., et al. 1995. J. Biol. Chem. 270: 12518-12525; Aalto Setälä K., Weinstock P. H., Bisgaier C. L., Lin Wu, Smith J. D. and Breslow J. L., 1996. Journal of Lipid Research, 37, 1802-1811] showing that the heterozygosity for a dysfunctional allele of LPL can contribute towards hypertriglyceridaemia, but with a low rate of occurrence in the population. The plasmatic concentration of apolipoprotein CIII (apo CIII), regulated by the expression of the gene apo CIII, possibly associated with a secondary cause, may be a novel and more frequent cause of hypertriglyceridaemia in man [Weinstock P. H., C. L. Bisgaier, K. Aalto-Setälä, H. Radner, R. Ramakrishnan, S. Levak-Frank, A. D. Essenburg, R. Zechner, and J. L. Breslow, 1995. J. Clin. Invest. 96: 2555-2568].

Apo CIII is a component of very low density lipoproteins (VLDLs), chylomicrons and high density lipoproteins (HDLs).

Many studies show that apo CIII plays an important role in the metabolism of triglyceride-rich lipoproteins (TGRLs). Clinical studies show a strong correlation between plasmatic apo CIII and the concentration of triglycerides [Schonfeld. G., P. K. George, J. Miller, P. Reilly, and J. Witztum, 1979. 28: 1001-1010; Shoulders C. C., et al. 1991. Atherosclerosis 87: 239-247; Le N-A., J. C. Gibson and H. N. Ginsberg, 1988. J. Lipid Res. 29: 669-677]. Furthermore, epidemiological studies show an association between certain alleles of apo CIII and the concentration of triglycerides [Rees A., J. Stocks, C. R. Sharpe, M. A. Vella, C. C. Shoulders, J. Katz, N. I. Jowett, F. E. Baralle, and D. J. Galton, 1985 J. Clin. Invest. 76: 1090-1095; Aalto-Setälä, et al. 1987. Atherosclerosis 66: 145-152; Tas, S. 1989. Clin. Chem. 35: 256-259; Ordovas J. M., et al. 1991. Atherosclerosis 87: 75-86; Ahn, Y. I., et al. 1991. Hum. Hered 41: 281-289; Zeng Q., M. Dammerman, Y. Takada, A. Matsunage, J. I. Breslow and J. Sasaki, 1994. Hum. Genet. 95: 371-375].

Apo CIII has the capacity to inhibit the activity of lipoprotein lipase (LPL) [C. S. Wang, W. J. McConnathy, H. U. Kloer and P. Alaupovic, J. Clin. Invest., 75, 384 (1984)] and to reduce the removal of "remnants" of the triglyceride-rich lipoproteins (TGRLs) via apolipoprotein E receptors [F. Shelburne, J. Hanks, W. Meyers and S. Quarfordt, J. Clin. Invest., 65, 652 (1980); E. Windler and R. J. Havel, J. Lipid Res., 26, 556, (1985)]. In apo CIII-deficient patients, the catabolism of TGRLs is accelerated [H. N. Ginsberg, N. A. Le, I. A. Goldberg, J. C. Gibson, A. Rubinstein, P. Wang-Iverson, R. Norum and W. V. Brown, J. Clin. Invest., 78, 1287 (1986)]. Conversely, the overexpression of human apo CIII in transgenic mice is associated with a severe hypertriglyceridaemia [Y. Ito, N. Azrolan, A. O'Connell, A. Walsh and J. L. Breslow, Science, 249, 790 (1990)].

Via these mechanisms, apo CIII brings about a reduction in the catabolism of TGRLs leading to an increase in the concentration of triglycerides. The reduction in the plasmatic concentration of apo CIII thus appears to be of certain value when a decrease in triglyceridaemia is desired as a therapeutic objective in at-risk populations.

The compounds of the invention are dihydrobenzodiazepines that are capable of reducing the secretion of apo CIII.

The compounds of the invention are of formula I:

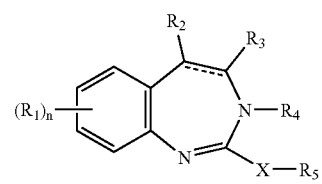

in which the dashed lines indicate the possible presence of a double bond;

$R_1$ represents optionally halogenated $(C_1-C_{18})$alkyl, optionally halogenated $(C_1-C_{18})$alkoxy, halogen, nitro, hydroxyl or $(C_6-C_{10})$aryl (optionally substituted with optionally halogenated $(C_1-C_6)$alkyl, optionally halogenated $(C_1-C_6)$alkoxy, halogen, nitro or hydroxyl);

n represents 0, 1, 2, 3 or 4;

$R_2$ and $R_3$ represent, independently of each other, hydrogen; optionally halogenated $(C_1$-$C_{18})$alkyl; $(C_1$-$C_{18})$alkoxy; $(C_6$-$C_{10})$aryl; $(C_6$-$C_{10})$aryl$(C_1$-$C_6)$alkyl; heteroaryl; heteroaryl$(C_1$-$C_6)$alkyl; $(C_6$-$C_{10})$aryloxy; $(C_6$-$C_{10})$aryl$(C_1$-$C_6)$alkoxy; heteroaryloxy; or heteroaryl$(C_1$-$C_6)$alkoxy; in which heteroaryl represents a 5- to 7-membered aromatic heterocycle containing one, two or three endocyclic hetero atoms chosen from O, N and S, and in which the aryl and heteroaryl portions of these radicals are optionally substituted with halogen, optionally halogenated $(C_1$-$C_6)$alkoxy, optionally halogenated $(C_1$-$C_6)$alkyl, nitro and hydroxyl;

$R_4$ represents hydrogen, $(C_1$-$C_{18})$alkyl or $(C_6$-$C_{10})$aryl, the said aryl group optionally being substituted with halogen, optionally halogenated $(C_1$-$C_6)$alkoxy, optionally halogenated $(C_1$-$C_6)$alkyl, nitro or hydroxyl;

X represents S, O or —NT in which T represents a hydrogen atom, $(C_1$-$C_6)$alkyl, $(C_6$-$C_{10})$aryl, $(C_6$-$C_{10})$aryl$(C_1$-$C_6)$alkyl or $(C_6$-$C_{10})$arylcarbonyl;

$R_5$ represents $(C_1$-$C_{18})$alkyl; hydroxy$(C_1$-$C_{18})$alkyl; $(C_6$-$C_{10})$aryl$(C_1$-$C_6)$alkyl; $(C_3$-$C_8)$cycloalkyl$(C_1$-$C_6)$alkyl; $(C_5$-$C_8)$cycloalkenyl-$(C_1$-$C_6)$alkyl; isoxazolyl$(C_1$-$C_6)$alkyl optionally substituted with $(C_1$-$C_6)$alkyl; a group —$CH_2$—$CR_a$=$CR_bR_c$ in which $R_a$, $R_b$ and $R_c$ are chosen independently from $(C_1$-$C_{18})$alkyl, $(C_2$-$C_{18})$alkenyl, hydrogen and $(C_6$-$C_{10})$aryl; a group —$CH_2$—CO—Z in which Z represents $(C_1$-$C_{18})$alkyl, $(C_1$-$C_6)$alkoxycarbonyl, $(C_6$-$C_{10})$aryl$(C_1$-$C_6)$alkyl, $(C_6$-$C_{10})$aryl optionally fused to a 5- to 7-membered aromatic or unsaturated heterocycle comprising one, two or three endocyclic hetero atoms chosen from O, N and S; or 5- to 7-membered heteroaryl containing one, two or three endocyclic hetero atoms chosen from O, N and S; the aryl and heteroaryl portions of these radicals optionally being substituted with halogen, hydroxyl, optionally halogenated $(C_1$-$C_6)$alkyl, optionally halogenated $(C_1$-$C_6)$alkoxy, nitro, di$(C_1$-$C_6)$alkoxy-phosphoryl$(C_1$-$C_6)$alkyl or $(C_6$-$C_{10})$aryl (optionally substituted with halogen, optionally halogenated $(C_1$-$C_6)$alkyl, optionally halogenated $(C_1$-$C_6)$alkoxy, nitro or hydroxyl);

or alternatively $R_4$ and $R_5$ together form a group —$CR_6$=$CR_7$— in which $CR_6$ is linked to X and in which:

$R_6$ represents a hydrogen atom; $(C_1$-$C_{18})$alkyl; $(C_3$-$C_8)$cycloalkyl; $(C_6$-$C_{10})$aryl; carboxy$(C_1$-$C_6)$alkyl; $(C_1$-$C_6)$alkoxycarbonyl$(C_1$-$C_6)$alkyl; heteroaryl; $(C_1$-$C_6)$aryl$(C_1$-$C_6)$alkyl; and heteroaryl$(C_1$-$C_6)$alkyl; in which heteroaryl represents a 5- to 7-membered aromatic heterocycle containing one, two or three endocyclic hetero atoms chosen from O, N and S and in which the aryl and heteroaryl portions of these radicals are optionally substituted with $(C_1$-$C_6)$alkyl, $(C_1$-$C_6)$alkoxy, hydroxyl, nitro, halogen or di$(C_1$-$C_6)$alkoxy-phosphoryl $(C_1$-$C_6)$alkyl;

$R_7$ represents a hydrogen atom; hydroxyl; di$(C_1$-$C_6)$alkylamino$(C_1$-$C_6)$alkyl; $(C_1$-$C_{18})$alkyl; carboxyl; $(C_1$-$C_6)$alkoxycarbonyl; $(C_6$-$C_{10})$aryl; heteroaryl; $(C_6$-$C_{10})$aryl$(C_1$-$C_6)$alkyl; or heteroaryl$(C_1$-$C_6)$alkyl; in which heteroaryl represents a 5- to 7-membered aromatic heterocycle containing one, two or three endocyclic hetero atoms chosen from O, N and S and in which the aryl and heteroaryl portions of these radicals are optionally substituted with halogen, hydroxyl, optionally halogenated $(C_1$-$C_6)$alkyl, optionally halogenated $(C_1$-$C_6)$alkoxy, carboxyl, $(C_1$-$C_6)$alkoxy-carbonyl, nitro, di$(C_1$-$C_6)$alkoxyphosphoryl$(C_1$-$C_6)$alkyl, $(C_6$-$C_{10})$aryl(this radical optionally being substituted with hydroxyl, nitro, optionally halogenated $(C_1$-$C_6)$alkyl, optionally halogenated $(C_1$-$C_6)$alkoxy or halogen) or $(C_6$-$C_{10})$aryl fused to a 5- to 7-membered aromatic or unsaturated heterocycle comprising one, two or three endocyclic hetero atoms chosen from O, N and S;

or alternatively $R_6$ and $R_7$ together form a $C_3$-$C_6$ alkylene chain optionally interrupted with a nitrogen atom which is optionally substituted with $(C_1$-$C_6)$alkyl or $(C_6$-$C_{10})$aryl or $(C_6$-$C_{10})$aryl$(C_1$-$C_6)$alkyl, (the aryl portions of these radicals optionally being substituted with halogen, nitro, hydroxyl, optionally halogenated $(C_1$-$C_6)$alkyl or optionally halogenated $(C_1$-$C_6)$alkoxy).

It should be understood that the compounds of formula I in which X=S; n=0; $R_2$ represents methyl and $R_3$ represents a hydrogen atom; $R_4$ and $R_5$ together form a group —$CR_6$=$CR_7$— in which $CR_6$ is linked to X, $R_6$ and $R_7$ together form a —$(CH_2)_3$— or —$(CH_2)_4$-chain or alternatively $R_6$ represents a hydrogen atom or a propyl group and $R_7$ is a phenyl group optionally substituted with —$OCH_3$ or a hydroxyl group, are excluded from the context of the invention.

The pharmaceutically acceptable salts of the compounds of formula I with acids or bases also form part of the invention.

J. Heterocycl. Chem. 1969, 6 (4), 491 describes benzodiazepine derivatives whose structure is similar to that of tetramisole (DL-2,3,5,6-tetrahydro-6-phenylimidazo[2,1-b]thiazole hydrochloride) which is a powerful anthelmintic agent. Among these compounds, those whose structure corresponds to formula I above have been excluded, by disclaimer, from the context of the invention.

The invention is directed not only towards the compounds of formula I but also to the salts thereof.

When the compound of formula I comprises an acid function, and for example a carboxylic function, it can form a salt with a mineral or organic base.

As examples of salts with organic or mineral bases, mention may be made of the salts formed with metals and especially with alkali metals, alkaline-earth metals and transition metals (such as sodium, potassium, calcium, magnesium and aluminium) or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

When the compound of formula I comprises a basic function, and, for example, a nitrogen atom, it can form a salt with an organic or mineral acid.

The salts with organic or mineral acids are, for example, the hydrochloride, hydrobromide, sulphate, hydrogen sulphate, dihydrogen phosphate, citrate, maleate, fumarate, 2-naphthalenesulphonate and para-toluenesulphonate.

The invention also covers salts allowing a suitable separation or crystallization of the compounds of formula I, such as picric acid, oxalic acid or an optically active acid, for example tartaric acid, dibenzoyltartaric acid, mandelic acid or camphorsulphonic acid.

Formula I encompasses all the types of geometric isomers and stereoisomers of the compounds of formula I.

According to the invention, the term "alkyl" denotes a linear or branched hydrocarbon-based radical preferably containing from 1 to 18 carbon atoms, better still from 1 to 12 carbon atoms, for example from 1 to 10 and especially from 1 to 6. Examples of these are especially methyl, ethyl, propyl, isopropyl, butyl, tert-butyl, isobutyl, pentyl, hexyl, heptyl, octyl, nonyl, decyl, undecyl, dodecyl, tridecyl, tetradecyl, pentadecyl, hexadecyl, heptadecyl and octadecyl groups.

The term "alkoxy" denotes an alkyl group as defined above linked to an oxygen atom. Examples of these are methoxy, ethoxy, isopropyloxy, butoxy and hexyloxy radicals.

The expression "optionally halogenated" means optionally substituted with one or more halogen atoms.

When the alkyl group is optionally halogenated, it preferably represents perfluoroalkyl and especially pentafluoroethyl or trifluoromethyl.

When the alkoxy group is halogenated, it preferably represents —O—$CHF_2$ or is perfluorinated. Examples of perfluorinated radicals are —$OCF_3$ and —O—$CF_2$—$CF_3$.

The expression "alkylene group" means linear or branched alkylene groups, that is to say divalent radicals which are linear or branched divalent alkyl chains.

The term "cycloalkyl" denotes saturated hydrocarbon-based groups which may be mono- or polycyclic and preferably contain from 3 to 18 carbon atoms, better still from 3 to 12 carbon atoms, for example from 3 to 8.

The polycyclic cycloalkyl groups consist of monocycles fused in pairs (for example ortho-fused or peri-fused), that is to say ring pairs containing at least two carbon atoms in common.

Monocyclic cycloalkyl groups such as cyclopropyl, cyclobutyl, cyclopentyl, cyclohexyl, cycloheptyl, cyclooctyl, cyclononyl, cyclodecyl, cycloundecyl and cyclododecyl are more particularly preferred.

Among the polycyclic cycloalkyls, mention may be made of adamantyl, norbornyl or the group of formula:

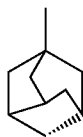

According to the invention, the term "cycloalkenyl" means a cycloalkyl group as defined above, containing one or more double bonds, preferably one double bond.

The term "halogen" means a fluorine, chlorine, bromine or iodine atom.

The term "alkenyl" means a linear or branched hydrocarbon-based chain comprising one or more double bonds. Examples of alkenyl groups that are particularly preferred are alkenyl groups bearing only one double bond, such as —$CH_2$—$CH_2$—CH=C($CH_3$)$_2$, vinyl or allyl.

The term "aryl" represents a mono- or polycyclic aromatic hydrocarbon-based group preferably containing from 6 to 18 carbon atoms, for example from 6 to 14 carbon atoms and especially from 6 to 10 carbon atoms.

Each polycyclic aryl group comprises two or more monocyclic aromatic nuclei, fused in pairs, that is to say having ring pairs containing at least two carbon atoms in common.

Preferred examples of polycyclic aromatic groups are bicyclic, tricyclic and tetracyclic groups.

Among these, mention may be made of phenyl, naphthyl, anthryl, phenanthryl, pyrenyl, chrysenyl and naphthacenyl groups.

The term "heteroaryl" denotes a mono- or polycyclic aromatic radical comprising one or more hetero atoms chosen from O, N, S and P. Preferably, the heteroaryl comprises 1 to 3 hetero atoms chosen from O, N and S.

When the radical is a polycyclic aromatic radical, it consists of two or more aromatic monocyclic nuclei fused in pairs, each monocyclic nucleus possibly comprising one or more endocyclic hetero atoms.

Preferably, the polycyclic heteroaryl radical is bicyclic or tricyclic.

Advantageously, the monocyclic heteroaryl group and the monocyclic nuclei forming the polycyclic heteroaryl are 5- to 7-membered. Examples of monocyclic heteroaryls are furyl, thienyl, pyrrolyl, oxazolyl, isoxazolyl, thiazolyl, isothiazolyl, imidazolyl, pyrazolyl, oxadiazolyl, triazolyl, thiadiazolyl, pyridyl, pyridazinyl, pyrazinyl and triazinyl groups.

Examples of polycyclic heteroaryls are indolizine, indole, isoindole, benzofuran, benzothiophene, indazole, benzimidazole, benzothiazole, purine, quinolizine, quinoline, isoquinoline, cinnoline, phthalazine, quinazoline, quinoxaline, naphthyridine, pteridine, pyrazolotriazine, thiazolopyrimidine, pyrazolopyrimidine, carbazole, acridine, phenazine, phenothiazine, phenoxazine or the group of formula:

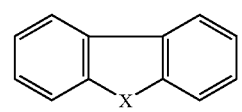

in which X is O or S.

An example of heteroaryl is ($C_6$-$C_{18}$)aryl fused to an aromatic heterocycle such as a 5- to 7-membered aromatic heterocycle comprising 1, 2 or 3 endocyclic hetero atoms chosen from O, N and S.

The expression "saturated or unsaturated heterocycle" means a mono- or polycyclic group comprising one or more hetero atoms chosen from O, N, S and P. The heterocycle preferably comprises one to three hetero atoms chosen from O, N and S. When the heterocycle is polycyclic, it comprises two or more saturated or unsaturated monocyclic nuclei that are preferably 5- to 7-membered, fused in pairs.

When the heterocycle is monocyclic, it is 5- to 7-membered.

Among the polycyclic heterocycles, bicyclic or tricyclic heterocycles are preferred.

Examples of saturated heterocycles are tetrahydrofuran, tetrahydrothiophene, tetrahydro-pyrrole, tetrahydrooxazole, dioxolane, tetrahydro-thiazole, tetrahydroimidazole, tetrahydropyrazole, tetrahydroisoxazole, tetrahydroisothiazole, tetrahydro-oxadiazole, tetrahydrotriazole, tetrahydrothiadiazole, piperidine, dioxane, morpholine, dithiane, thiomorpholine, piperazine and trithiane.

Among the saturated heterocycles, mention may also be made of the saturated derivatives of the polycyclic heteroaryls listed above as preferred radicals.

Examples of unsaturated heterocycles are the unsaturated derivatives of the saturated heterocycles mentioned above and also the unsaturated derivatives of the heteroaryls mentioned above.

The expression "unsaturated heterocycle" means a non-aromatic heterocycle comprising one or more unsaturations of ethylenic type.

Preferably, the unsaturated heterocycle comprises only one double bond. Preferred examples of unsaturated heterocycles are dihydrofuryl, dihydrothienyl, dihydropyrrolyl, pyrrolinyl, oxazolinyl, thiazolinyl, imidazolinyl, pyrazolinyl, isoxazolinyl, isothiazolinyl, oxadiazolinyl, pyranyl and unsaturated mono-derivatives of piperidine, of dioxane, of piperazine, of trithiane, of morpholine, of dithiane and of thiomorpholine, and also tetrahydropyridazinyl, tetrahydropyrimidinyl and tetrahydrotriazinyl.

When Z or $R_7$ comprises or represents $(C_6-C_{10})$aryl optionally fused to an unsaturated heterocycle optionally substituted with oxo, the unsaturated heterocycle preferably contains at least one unsaturation in common with the aryl group.

Examples of such aryl groups fused to an unsaturated heterocycle are, especially:

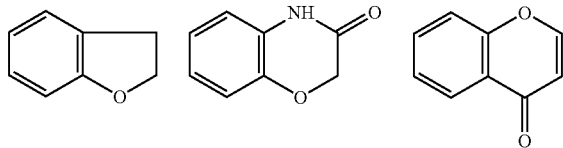

When Z or $R_7$ comprises a group of formula:

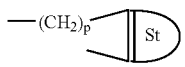

p preferably represents 0 or 1 and St preferably represents phenyl.

Preferably, the extremities 1 and 2 of this radical are attached to two adjacent carbon atoms of the said aryl, heterocycle, cycloalkyl or heteroaryl portion. Preferably, St represents phenyl. Examples which may be mentioned are the radical Z of formula:

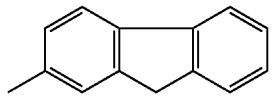

of Example 133 below: and the radical $R_7$ of formula:

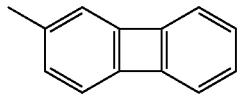

of Example 119 below.

According to the invention, the expression "optionally substituted with" generally means "optionally substituted with one or more of the radicals mentioned".

By way of example, when $R_1$ represents $(C_6-C_{10})$aryl, the aryl group is optionally substituted with one or more radicals chosen from:

optionally halogenated $(C_1-C_6)$alkyl;
$(C_1-C_6)$alkoxy;
halogen;
nitro; and
hydroxyl.

Nevertheless, the number of substituents is limited by the possible number of substitutions.

Thus, when $R_6$ and $R_7$ together form an alkylene chain interrupted with a nitrogen atom, this atom can be substituted with only one radical chosen from alkyl, aryl and arylalkyl.

A first group of compounds of the invention consists of bicyclic derivatives in which $R_4$ and $R_5$ do not together form a group —$CR_6$=$CR_7$—.

A second group of compounds of the invention consists of bicyclic derivatives in which $R_4$ and $R_5$ together form a group —$CR_6$=$CR_7$—, it being understood that $R_6$ and $R_7$ do not together form an alkylene chain optionally interrupted with a nitrogen atom.

A third group of compounds of the invention consists of tetracyclic derivatives in which $R_4$ and $R_5$ together form a group —$CR_6$=$CR_7$— in which $R_6$ and $R_7$ together form an alkylene chain optionally interrupted with a nitrogen atom.

When $R_6$ and $R_7$ together form an alkylene chain optionally interrupted with a nitrogen atom, the ring formed by $CR_6$=$CR_7$ may be fused to a $(C_6-C_{18})$aryl group optionally substituted with one or more Su groups.

Preferably, $CR_6$=$CR_7$ forms the group:

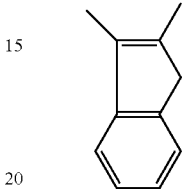

According to the invention, a first group of preferred compounds (group 1) consists of compounds of formula I in which X represents —NT in which T is as defined above and $R_4$ and $R_5$ together form —$CR_6$=$CR_7$—.

Among these compounds, the ones that are preferred are those in which $R_6$ represents a hydrogen atom; and $R_7$ represents hydroxyl; or $(C_6-C_{10})$aryl optionally substituted with halogen, nitro, hydroxyl, optionally halogenated $(C_1-C_6)$alkyl or $(C_1-C_6)$alkoxy.

Most particularly, $R_7$ is chosen from hydroxyl and phenyl.

Preferred meanings of T are a hydrogen atom and $(C_1-C_6)$alkyl, for example methyl.

A second group of preferred compounds (group 2) consists of compounds of formula I in which X represents S;
$R_4$ represents a hydrogen atom;
$R_5$ represents —$CH_2$—$CR_a$=$CR_bR_c$ in which $R_a$ is a hydrogen atom, $(C_1-C_6)$alkyl or $(C_6-C_{10})$aryl, $R_b$ is $(C_1-C_6)$alkyl or a hydrogen atom and $R_c$ represents a hydrogen atom or $(C_2-C_{10})$alkenyl; a group —$CH_2$—CO—Z in which Z represents $(C_1-C_{10})$alkyl, $(C_6-C_{10})$aryl$(C_1-C_6)$alkyl, 5- or 6-membered heteroaryl or $(C_6-C_{10})$aryl optionally fused to a 5- to 7-membered aromatic or unsaturated heterocycle; the aryl and heteroaryl portions of these radicals optionally being substituted with halogen, hydroxyl, $(C_1-C_6)$alkyl, $(C_1-C_6)$alkoxy, nitro or $(C_6-C_{10})$aryl (optionally substituted with halogen, optionally halogenated $(C_1-C_6)$alkyl, optionally halogenated $(C_1-C_6)$alkoxy or nitro); $(C_1-C_6)$alkyl; hydroxy $(C_1-C_6)$alkyl; $(C_6-C_{10})$aryl$(C_1-C_6)$alkyl; $(C_5-C_8)$cycloalkenyl$(C_1-C_6)$alkyl; or isoxazolyl$(C_1-C_6)$alkyl optionally substituted with one or more $(C_1-C_6)$alkyls;

or alternatively $R_4$ and $R_5$ together form a group —$CR_6$=$CR_7$— in which $R_6$ represents a hydrogen atom, $(C_1-C_6)$alkyl, $(C_6-C_{10})$ aryl (optionally substituted with halogen, hydroxyl, nitro, $(C_1-C_6)$alkyl or $(C_1-C_6)$alkoxy), carboxy$(C_1-C_6)$alkyl, or $(C_1-C_6)$alkoxy-carbonyl $(C_1-C_6)$alkyl; and $R_7$ represents a hydrogen atom; hydroxyl; di$(C_1-C_6)$alkylamino$(C_1-C_6)$alkyl; $(C_1-C_{10})$alkyl; $(C_1-C_6)$alkoxycarbonyl; $(C_6-C_{10})$aryl; heteroaryl; $(C_6-C_{10})$aryl$(C_1-C_6)$alkyl; the aryl and heteroaryl portions of these radicals optionally being substituted with $(C_1-C_6)$alkoxycarbonyl, halogen, hydroxyl, $(C_1-C_6)$alkyl, $(C_6-C_{10})$aryl, (this radical optionally being substituted with halogen, optionally halogenated $(C_1-C_6)$ alkyl, $(C_1-C_6)$alkoxy or nitro) or $(C_6-C_{10})$aryl fused to a 5- to 7-membered aromatic or unsaturated heterocycle comprising one, two or three endocyclic hetero atoms chosen from O, N and S); or alternatively $R_6$ and $R_7$ together form an alkylene chain interrupted with a nitrogen atom optionally substituted with $(C_6\text{-}C_{10})$aryl$(C_1\text{-}C_6)$alkyl in which the aryl portion is optionally substituted with halogen, optionally halogenated $(C_1\text{-}C_6)$alkyl, $(C_1\text{-}C_6)$alkoxy, hydroxyl or nitro.

Among these compounds, the ones that are especially preferred are those in which one or more of the substituents $R_4$, $R_5$, $R_6$ and $R_7$ are defined as follows:

$R_5$ represents —$CH_2$—$CR_a$=$CR_bR_c$ in which $R_a$ is $(C_1\text{-}C_6)$alkyl, phenyl or a hydrogen atom, $R_b$ is $(C_1\text{-}C_6)$alkyl or a hydrogen atom and $R_c$ represents a hydrogen atom or a monounsaturated $(C_2\text{-}C_{10})$alkenyl; a group —$CH_2COZ$ in which Z represents $(C_1\text{-}C_{10})$alkyl, benzyl, $(C_1\text{-}C_6)$alkoxycarbonyl, phenyl (optionally substituted with phenyl or hydroxyl), naphthyl, phenyl fused to dihydrofuryl, to dihydrothienyl or to dihydropyrrolyl, furyl, thienyl or pyrrolyl; $(C_1\text{-}C_6)$alkyl; hydroxy-$(C_1\text{-}C_6)$alkyl; benzyl; $(C_3\text{-}C_8)$cycloalkenyl$(C_1\text{-}C_6)$alkyl; or isoxazolyl$(C_1\text{-}C_6)$alkyl optionally substituted with $(C_1\text{-}C_6)$alkyl;

$R_4$ and $R_5$ together form —$CR_6$=$CR_7$— in which either $R_6$ or $R_7$, or both of them, are as defined below in (i), (ii) or (iii):

(i) $R_6$ represents a hydrogen atom; $(C_1\text{-}C_6)$alkyl; phenyl optionally substituted with halogen, $(C_1\text{-}C_6)$alkyl, $(C_1\text{-}C_6)$alkoxy, hydroxyl or nitro; carboxy-$(C_1\text{-}C_6)$alkyl; or $(C_1\text{-}C_6)$alkoxycarbonyl$(C_1\text{-}C_6)$alkyl;

(ii) $R_7$ represents a hydrogen atom; hydroxyl; di$(C_1\text{-}C_6)$alkylamino$(C_1\text{-}C_6)$alkyl; $(C_1\text{-}C_{10})$alkyl; $(C_1\text{-}C_6)$alkoxycarbonyl; naphthyl; phenyl optionally substituted with halogen, $(C_1\text{-}C_6)$alkoxycarbonyl, hydroxyl, phenyl (itself optionally substituted with halogen, hydroxyl, optionally halogenated $(C_1\text{-}C_6)$alkyl, $(C_1\text{-}C_6)$alkoxy, $(C_1\text{-}C_6)$alkoxycarbonyl or nitro) or phenyl fused to dihydrofuryl, dihydrothienyl or dihydropyrrolyl; pyridyl; furyl; thienyl; pyrrolyl; or benzyl;

(iii) $R_6$ and $R_7$ together form an alkylene chain interrupted with a nitrogen atom optionally substituted with phenyl$(C_1\text{-}C_6)$alkyl in which the alkyl portion is optionally substituted with halogen.

Among the preferred compounds of groups 1 and 2, it is preferable for at least one from among n, $R_1$, $R_2$ and $R_3$ to be as defined below:

$R_3$ represents a hydrogen atom;
$R_2$ represents a hydrogen atom or a $(C_6\text{-}C_{10})$aryl group optionally substituted with halogen, $(C_1\text{-}C_6)$alkoxy, optionally halogenated $(C_1\text{-}C_6)$alkyl, nitro or hydroxyl;
$R_1$ represents a halogen atom;
n represents 0, 1 or 2, and better still n represents 0 or 1. More preferably, n is 0.

The compounds of Examples 1 to 67 below are preferred.

Among these compounds, ones most particularly preferred are:

3-(biphenyl-4-yl)-5,6-dihydrothiazolo[2,3-b]-1,3-benzodiazepine (Example 4);

3-(2-furyl)-5,6-dihydrothiazolo[2,3-b]-1,3-benzodiazepine (Example 43);

3-[4-(ethoxycarbonyl)phenyl]-5,6-dihydro-thiazolo-[2,3-b]-1,3-benzodiazepine (Example 36);

1-(2-furyl)-2-(4,5-dihydro-3H-1,3-benzodiazepine-2-ylsulphamyl)ethanone (Example 14);

1-(biphenyl-4-yl)-2-(4,5-dihydro-3H-1,3-benzodiazepine-2-ylsulphamyl)ethanone (Example 5);

3-(biphenyl-3-yl)-5,6-dihydrothiazolo[2,3-b]-1,3-benzodiazepine (Example 38);

1-(3,4-dihydroxyphenyl)-2-(4,5-dihydro-3H-1,3-benzodiazepine-2-ylsulphamyl)ethanone (Example 29);

3-(3,4-dihydroxyphenyl)-5,6-dihydro-thiazolo[2,3-b]-1,3-benzodiazepine (Example 59); and 3-(biphenyl-4-yl)-7-chloro-5,6-dihydro-thiazolo[2,3-b]-1,3-benzodiazepine (Example 66).

The compounds of formula I may be prepared simply using one of the processes below.

A) In the case of the compounds of formula I in which X represents S, $R_4$ and $R_5$ do not together form —$CR_6$=$CR_7$— and dashed lines represent nothing.

These compounds may be prepared simply by reacting a thione of formula II:

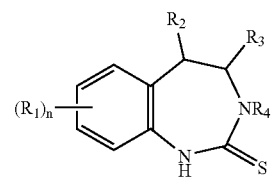

II in which:

n, $R_1$, $R_2$, $R_3$ and $R_4$ are as defined above for formula I, with a halo derivative of formula III:

Hal$^1$-$R_5$     III in which Hal$^1$ represents a halogen atom, $(C_1\text{-}C_6)$alkylsulphonyl in which the alkyl portion is optionally halogenated or $(C_6\text{-}C_{10})$arylsulphonyl in which the aryl portion is optionally substituted with $(C_1\text{-}C_6)$alkyl; and $R_5$ is as defined above for formula I.

Advantageously, Hal$^1$ represents halogen, tosyl or mesyl. The reaction is preferably carried out in a polar solvent which is inert towards the reagents.

A suitable solvent is a linear or cyclic ether such as dialkyl ethers (diethyl ether or diisopropyl ether) or cyclic ethers (such as tetrahydrofuran or dioxane) or alternatively polyethers of the type such as dimethoxyethane or diethylene glycol dimethyl ether.

The temperature at which the reaction is performed is generally between –20 and 70° C., preferably between 0 and 50° C. and better still between 15 and 35° C., for example at room temperature.

One particular case of application of this process is illustrated below for the preparation of compounds of formula I in which X represents S, $R_4$ is as defined above and $R_5$ represents —$CH_2$—CO—Z in which Z is as defined above for formula I.

According to this process, a thione of formula II is reacted, under the same conditions as above, with an α-halo ketone of formula IVa:

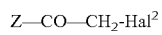

Z—CO—$CH_2$-Hal$^2$     Va in which Z is as defined above and Hal$^2$ represents a halogen atom. In the context of this particular embodiment, it is preferred to use mild reaction conditions such as, especially, a temperature of between 0 and 60° C. and preferably between 15 and 35° C.

When the compounds of formula I obtained by carrying out process A above are such that $R_4$ represents a hydrogen atom, the preparation of the corresponding compounds in which $R_4$ represents $(C_1\text{-}C_{18})$alkyl is readily performed by alkylation using a suitable alkylating agent.

Thus, the compound in which $R_4$=H may be reacted with a halo derivative of general formula $R_4$—X in which $R_4$ represents $(C_1$-$C_{18})$alkyl and X represents halogen, in the presence of a base.

Examples of bases that are particularly suitable are triethylamine, N-methylmorpholine, 4-(N,N-dimethylamino)pyridine, N,N-diethylamine, mineral bases of the type such as alkali metal hydroxides (NaOH or KOH), alkali metal carbonates ($NaHCO_3$ or $K_2CO_3$) and alkali metal hydrides such as NaH.

B) In the case of the compounds of formula I in which X represents S, $R_4$ and $R_5$ together form a group —$CR_6$=$CR_7$— and the dashed lines represent nothing.

These compounds may be prepared according to the invention, by reacting an α-halo ketone of formula IVb:

  IVb in which $R_6$ and $R_7$ are as defined above and $Hal^3$ represents a halogen atom, with a thione of formula IIa:

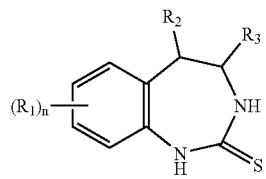  IIa in which $R_1$, n, $R_2$ and $R_3$ are as defined above for formula I, in a $C_2$-$C_6$ aliphatic carboxylic acid as solvent, at a temperature of between 90 and 130° C.

The exact implementation conditions will be determined by a person skilled in the art depending on the reactivity of the compounds present.

Examples of carboxylic acids which may be mentioned include acetic acid, propionic acid, butyric acid, pivalic acid and valeric acid.

It is possible, in the context of the invention, to perform the process in the presence of a mixture of solvents including one or more aliphatic carboxylic acids and optionally one or more other miscible polar solvents that are inert towards the compounds present.

Such additional solvents are, for example, $C_2$-$C_6$ monohydroxylated aliphatic alcohols such as ethanol, isopropanol and tert-butanol.

A preferred temperature range is from 100 to 125° C.

It may be convenient to perform the process at the reflux temperature of the solvent, and especially when the solvent used is acetic acid.

C) In the case of the compounds of formula I in which the dashed lines represent nothing, X represents NH, $R_4$ and $R_5$ together form —$CR_6$=$CR_7$— and $R_7$ is not a hydroxyl group.

According to the invention, these compounds may be prepared simply in two steps by carrying out the following process.

In a first step, a sulphide of formula V:

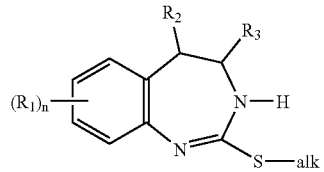  V in which $R_1$, n, $R_2$ and $R_3$ are as defined for formula I above and alk represents $(C_1$-$C_6)$alkyl, is reacted with a protected derivative of the acetone of formula VI:

  VI in which the carbonyl group of $R_6$ is protected with a protecting group that is labile in acidic medium, $R_6$ and $R_7$ being as defined above.

Examples of protecting groups for the carbonyl function, that are labile in acidic medium, are given in "Protective Groups in Organic Synthesis, Greene T. W. and Wuts P. G. M., published by John Wiley and Sons, 1991, and in Protecting Groups, Kocienski P. J., 1994, Georg Thieme Verlag.

In a particularly advantageous manner, the carbonyl group may be protected in the form of cyclic or non-cyclic ketal.

Thus, the protected derivative of the ketone of formula VI reacting with the sulphide V is preferably of formula VIa below:

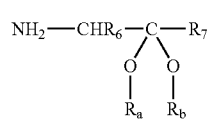  VIa in which $R_6$ and $R_7$ are as defined above for formula I and $R_a$ and $R_b$ are, independently, $(C_1$-$C_6)$alkyl or together form a linear or branched $(C_2$-$C_6)$alkylene chain, preferably a $(C_2$-$C_3)$alkylene chain.

The preferred ketals are especially 1,3-dioxolanes and methyl ketals.

Nevertheless, it may be envisaged to protect the carbonyl group with other protecting groups such as dithio and hemithio ketals or by formation of an enol ether, a thioenol ether, thiazolidines or imidazolidines.

The solvent used for this reaction is a polar solvent capable of dissolving the reagents present. A solvent which may thus be selected is a nitrile such as acetonitrile or isobutyronitrile.

When the reaction is carried out starting with the ketal VIa, the compound obtained after the first step is the compound of formula:

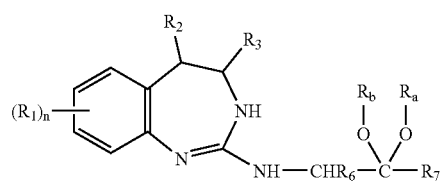  VII in which n, $R_1$, $R_2$, $R_3$, $R_6$, $R_7$, $R_a$ and $R_b$ are as defined above for formulae I and VIa. The compound resulting from the reaction II with the protected derivative of the ketone of formula VI, and, for example, compound VII above, is then treated in acidic medium so as to bring about the cyclization.

To this end, a Brönsted acid or a Lewis acid, a mineral acid or an organic acid may be used, without preference.

Examples of suitable acids are, especially, acetic acid, formic acid, oxalic acid, methanesulphonic acid, p-toluenesulphonic acid, trifluoroacetic acid, trifluoromethanesulphonic acid, Lewis acids such as boron trichloride, boron trifluoride, boron tribromide or hydrochloric acid.

The reaction is generally carried out at between 15 and 50° C., especially between 20 and 30° C.

The solvent used for the reaction depends on the acid used. When the acid is hydrochloric acid, the reaction is advantageously performed in a $(C_1\text{-}C_6)$alkanol such as ethanol.

The above process leads to the preparation of compounds of formula I in which T represents a hydrogen atom.

So as to synthesize the corresponding compound of formula I in which T represents $(C_1\text{-}C_6)$alkyl, $(C_6\text{-}C_{10})$aryl or $(C_6\text{-}C_{10})$aryl$(C_1\text{-}C_6)$alkyl, compound I obtained, for which T represents hydrogen, is reacted with a halo reagent of formula Hal-T in which T represents $(C_1\text{-}C_6)$alkyl, $(C_6\text{-}C_{10})$aryl or $(C_6\text{-}C_{10})$aryl$(C_1\text{-}C_6)$alkyl and Hal represents a halogen atom, in the presence of a suitable base.

Examples of bases are, especially, organic bases such as N-methylmorpholine, triethylamine, tributylamine, diisopropylethylamine, dicyclohexyl-amine, N-methylpiperidine, pyridine, 4-(1-pyrrolidinyl)pyridine, picoline, 4-(N,N-dimethylamino)-pyridine, N,N-dimethylaniline and N,N-diethylaniline.

The conditions for carrying out this reaction are known to those skilled in the art.

D) In the case of the compounds of formula I in which the dashed lines represent nothing, X represents —NT in which T is other than a hydrogen atom, $R_4$ and $R_5$ together form a group —$CR_6$=$CR_7$— and $R_7$ represents hydroxyl.

These compounds may be prepared by reacting a sulphide of formula V:

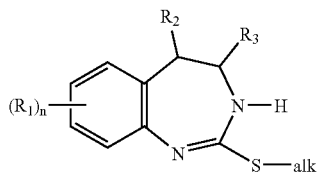

V in which n, $R_1$, $R_2$, $R_3$, $R_4$ and alk are as defined above, with a derivative of formula VIII:

VIII in which T and $R_6$ are as defined above for formula I and Y is a leaving group, at a temperature of between 50 and 150° C., preferably at a temperature of between 60 and 100° C.

Leaving groups which may be mentioned include a halogen atom, a $(C_1\text{-}C_6)$alkoxy group, an imidazolyl group and a $(C_6\text{-}C_{10})$aryl$(C_1\text{-}C_6)$alkoxy group.

This reaction is generally performed in a polar solvent and especially a nitrile such as acetonitrile or isobutyronitrile. Acetonitrile is preferably used as solvent.

E) In the case of the compounds of formula I in which the dashed lines represent nothing, X represents —NT, $R_4$ is not a hydrogen atom and $R_4$ and $R_5$ do not form —$CR_6$=$CR_7$—.

These compounds may be prepared by reacting a sulphide Va:

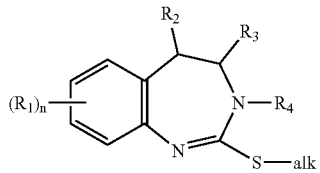

Va in which n, $R_1$, $R_2$, $R_3$, $R_4$ and alk are as defined above for formulae I and V, with an amine of formula IX:

IX in which T and $R_5$ are as defined above for formula I. This reaction is preferably performed at a temperature of between 15 and 50° C., for example between 20 and 30° C. in a solvent of the nitrile type such as acetonitrile or isobutyronitrile, acetonitrile being preferred.

F) In the case of the compounds of formula I in which the dashed lines represent nothing, X=S, $R_4$ and $R_5$ together form —$CR_6$=$CR_7$— and $R_7$ represents hydroxyl.

These compounds are readily prepared by reacting a thione of formula IIa:

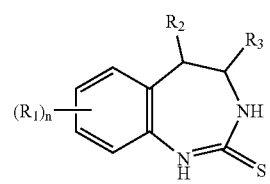

IIa in which n, $R_1$, $R_2$ and $R_3$ are as defined above for formula I, with a halo derivative of formula X:

X in which Hal$^4$ represents halogen and $R_6$ and Y are as defined above for formula VIII.

This reaction is preferably performed in a $C_6\text{-}C_{10}$ aromatic hydrocarbon of the type such as toluene or benzene. The temperature at which the reaction is performed is generally between 80 and 130° C., for example between 100 and 120° C. Preferred conditions are, for example, refluxing in toluene.

G) In the case of the compounds of formula I in which the dashed lines represent nothing, X=S and $R_4$ and $R_5$ together form —CH=CH—.

According to the invention, these compounds are prepared by reacting the thione below of formula XI:

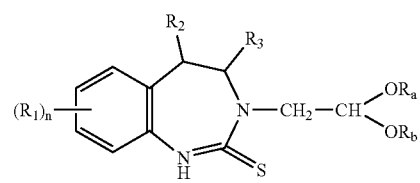

XI in which n, $R_1$, $R_2$, $R_3$, $R_a$ and $R_b$ are as defined above for formulae I and VII, with a strong acid such as sulphuric acid or hydrochloric acid, or alternatively with one of the acids listed above in the case of variant C.

According to this process, the reaction temperature required depends on the strength of the acid used.

Generally, a temperature of between 10 and 40° C. is sufficient, for example between 20 and 30° C.

This reaction may be performed in aqueous medium. In this case, the reaction medium obtained must be homogeneous.

H) In the case of the compounds of formula I in which the dashed lines represent nothing, X represents O and $R_4$ and $R_5$ together form —$CR_6$=$CR_7$—.

These compounds are prepared by thermal cyclization of a compound of formula XII:

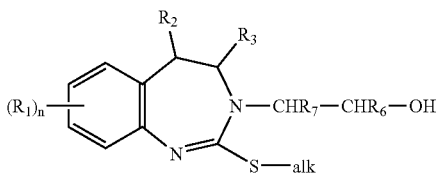

in which n, $R_1$, $R_2$, $R_3$, $R_6$ and $R_7$ are as defined above for formula I and alk represents $(C_1-C_6)$alkyl, followed by dehydrogenation of the resulting compound of formula XIII:

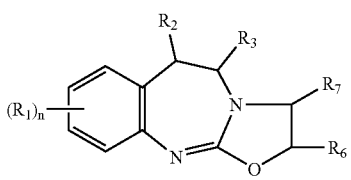

according to the standard processes of organic chemistry, so as to obtain the expected compound of formula I. The thermal cyclization may be performed, for example, in a $C_2-C_6$ monohydroxylated aliphatic alcohol such as ethanol, isopropanol or tert-butanol as solvent, at a temperature of between 80 and 160° C.

I) In the case of the compounds of formula I in which the dashed lines indicate the presence of a double bond.

These compounds are prepared by dehydrogenation of the corresponding compounds of formula I in which the dashed lines represent nothing.

This dehydrogenation reaction is performed in a manner that is known per se, for example by the action of:
- sulphur (cf. Organic Synthesis, Vol. 2, published by John Wiley & Sons, 1988, page 423; Organic Synthesis, Vol. 3, published by John Wiley & Sons, 1988, page 729);
- 5% palladium-on-charcoal in a refluxing decalin (cf. Organic Synthesis, Vol. 4, published by John Wiley & Sons, 1988, page 536);
- 2,3-dichloro-5,6-dicyano-1,4-benzoquinone or DDQ (cf. Organic Synthesis, Vol. 5, published by John Wiley & Sons, 1988, page 428; Synthesis, 1983, 310).

The thiones of formulae II and IIa are compounds that are readily prepared by organic synthesis from commercial products.

The thiones of formula IIa are thiones of formula II in which $R_4$ represents a hydrogen atom.

These compounds may especially be prepared by following and optionally by adapting any one of the processes described in:

Spindler Juergen; Kempter Gerhard; Z. Chem.; 27; 1. 1987; 36-37 or

Setescak Linda L.; Dekow Frederick W.; Kitzen Jan M.; Martin Lawrence L.; J. Med. Chem.; 27; 3; 1984; 401-404.

These two publications more particularly describe the synthesis of 1,3,4,5-tetrahydro-(1H,3H)-1,3-benzodiazepine-2-thione, 1,3,4,5-tetrahydro-(1H,3H)-4-phenyl-1,3-benzodiazepine-2-thione and 1,3,4,5-tetrahydro-(1H,3H)-3-methyl-4-phenyl-1,3-benzodiazepine-2-thione.

By way of example, when $R_2$ represents optionally substituted aryl or heteroaryl and $R_3$ represents H, one route for synthesizing the thione of formula II in which the dashed lines represent nothing is proposed in Scheme 1 below.

SCHEME 1

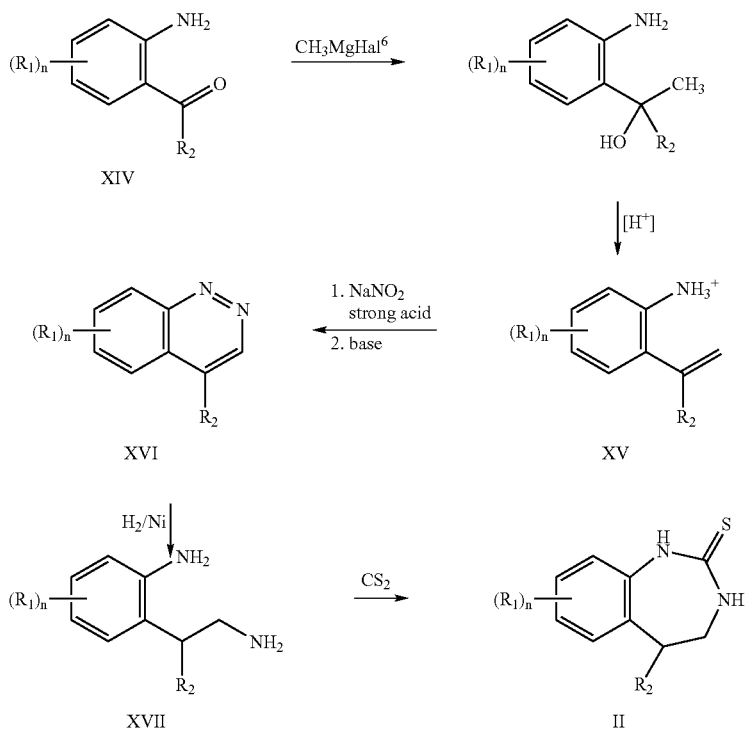

The ketone XIV is treated, under the usual conditions, with a Grignard reagent of formula $CH_3MgHal^6$ in which $Hal^6$ is a halogen atom. The process is performed, for example, in an ether, preferably an aliphatic ether such as diethyl ether or diisopropyl ether or tetrahydrofuran, at a temperature of between 20 and 50° C. and preferably between 30 and 40° C.

After dehydration of the intermediate alcohol (in acidic medium), compound XV is recovered in the form of a salt. The nature of the counterion in compound XV (which counterion is not represented in Scheme 1) depends on the acid used for the dehydration. In the next step, compound XV is treated with sodium nitrite in the presence of a strong acid such as hydrochloric acid, and the intermediate compound is then treated with a base and preferably with a hydroxide of the type such as an alkali metal hydroxide or ammonium hydroxide.

The diazo compound of formula XVI obtained is then subjected to a hydrogenation in the presence of nickel in a solvent of polar type such as a $(C_1-C_6)$alkanol or an amide of the type such as dimethylformamide, at a temperature of between 30 and 100° C. and preferably at a temperature of from 50 to 70° C.

The thione is finally prepared by reacting the hydrogenated compound XVII with carbon disulphide, under suitable conditions such as, for example, at reflux in a $C_1-C_6$ aliphatic alcohol, for example in refluxing ethanol.

Another process for preparing thiones of formula II in which $R_2$ and $R_3$ both represent a hydrogen atom and the dashed lines represent nothing is illustrated in Scheme 2 below.

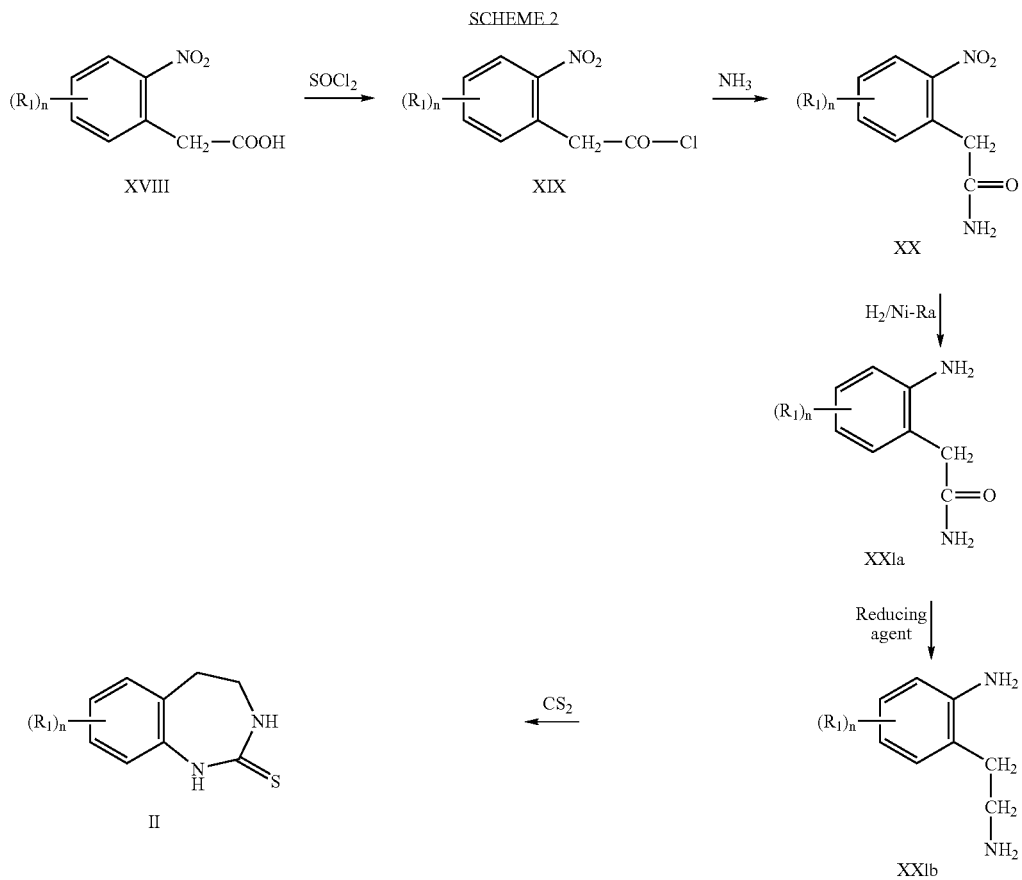

The amine of formula XXIa is prepared in a conventional manner by the action of thionyl chloride, followed by ammonia, and finally by catalytic hydrogenation in the presence of Raney nickel.

Next, the carbonyl function of compound XXIa is reduced by the action of a suitable reducing agent. Examples of suitable reducing agents are hydrides (such as lithium aluminium hydride, sodium borohydride, sodium cyanoborohydride, $BH_3/BF_3$-$Et_2O$ and $Et_3SiH$), zinc in hydrochloric acid medium, lithium in ammoniacal medium or Raney nickel in ethanolic medium.

The reduction may also be performed by catalytic hydrogenation, for example in the presence of palladium-on-charcoal or platinum oxide.

The process is preferably performed in the presence of $LiAlH_4$. The reduction of compound XXIa gives compound XXIb.

The amine XXIb is then reacted with carbon disulphide, preferably in a polar solvent of $C_1-C_6$ alkanol type (such as, for example, ethanol), at a temperature of between 80 and 150° C. at the end of the reaction.

The sulphides of formula Va are readily obtained from the corresponding thiones of formula II.

One possible synthetic route consists in reacting the appropriate thione of formula II:

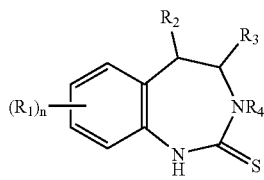

in which n, $R_1$, $R_2$, $R_3$ and $R_4$ are as defined above, with a halide $Hal^5$-alk in which $Hal^5$ represents a halogen atom and alk represents ($C_1$-$C_6$)alkyl, in a polar protic solvent such as an aliphatic alcohol, for example a ($C_1$-$C_6$)alkanol. It is strongly desirable that the alkyl chain of the alcohol used as solvent should correspond exactly to the alk chain of the halo derivative.

The reaction of the thione II with this halo derivative is preferably performed at a temperature of between 15 and 50° C. and preferentially between 20 and 30° C., for example at room temperature.

This process is particularly advantageous for the preparation of compounds of formula Va in which alk represents methyl.

Preferably, $Hal^5$ represents an iodine atom.

The compounds of formula XI in which $R_3$ represents a hydrogen atom may be prepared using the process illustrated in Scheme 3 below.

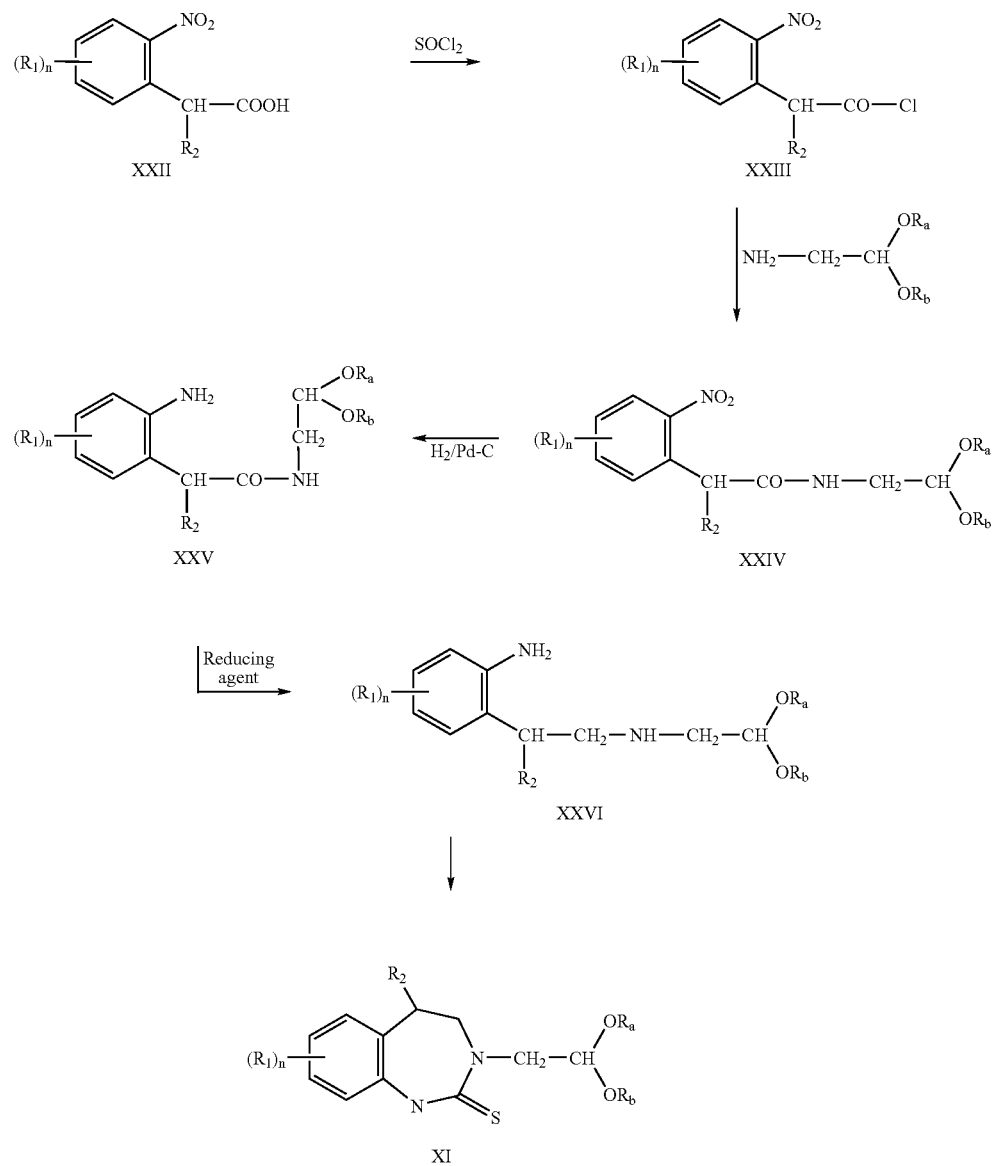

The amide of formula XXIV is prepared conventionally starting with the acid of formula XXII by the action of thionyl chloride and the appropriate amine of formula $NH_2$—$CH_2$—$CH(OR_a)(OR_b)$ in which $R_a$ and $R_b$ are as defined above for formula XI.

Next, the amide XXIV is subjected to a hydrogenation reaction in the presence of palladium-on-charcoal so as to convert the nitro function into an amine function. This conversion is performed under the standard conditions of organic chemistry.

The carbonyl function of the resulting amine is then reduced by the action of a suitable hydride, for example lithium aluminium hydride, sodium borohydride, sodium cyanoborohydride or diisobutylaluminium hydride.

Next, the amine obtained, XXVI, is treated with carbon disulphide under the same conditions described above in the case of compound XVII (Scheme 1) or in the case of compound XXIb (Scheme 2).

The compounds of formula XII in which $R_3$ represents hydrogen may be synthesized by carrying out the process illustrated in Scheme 4 below:

The amine of formula XXVII is prepared simply by reacting an amine of formula $NH_2$—$CHR_7$—$CHR_6$—OH, in which $R_6$ and $R_7$ are as defined above for formula I, with the acid chloride of formula XXIII. This reaction is carried out under the standard conditions, preferentially in the presence of a base, and preferably of an organic base. The next three steps, which lead to the compound of formula XXX, are carried out under conditions comparable to the case of the conversion of compound XXIV into compound XI (Scheme 3). Next, compound XXX is reacted with $Hal^7$-alk in which $Hal^7$ represents a halogen atom and alk is $(C_1$-$C_6)$alkyl. This reaction may be carried out under the conditions specified above for the conversion of the thione II into the sulphide of formula Va. This reaction is preferably performed in a $C_1$-$C_6$ alkanol whose alkyl chain corresponds exactly to the alk chain of alk-$Hal^7$ and with a halide alk-$Hal^7$ in which $Hal^7$ represents an iodine atom.

The hypolipidaemiant activity of the compounds of the invention result from their ability to reduce the secretion of apo CIII. The biological test which follows was developed so as to demonstrate this activity. It reveals the capacity of

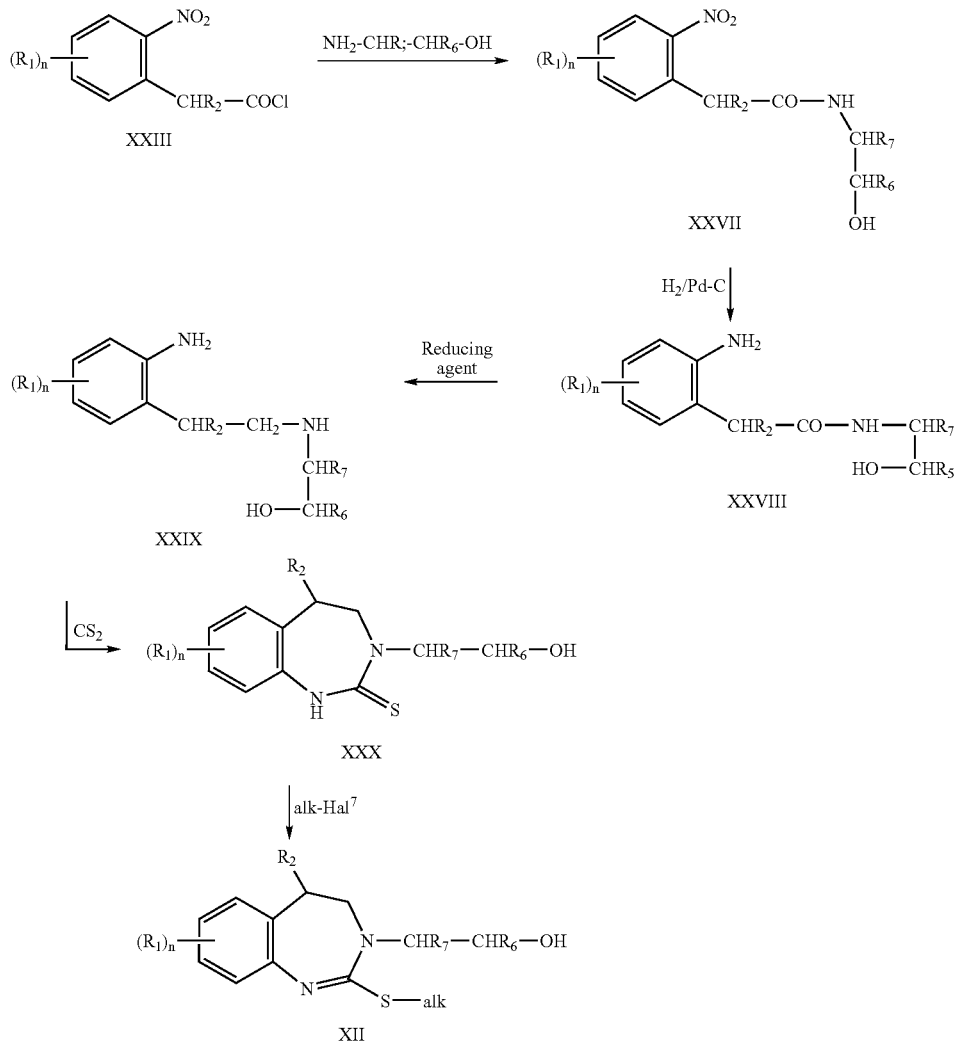

SCHEME 4 the compounds of the invention to reduce the secretion of apo CIII by a line of human hepatocytes Hep G2 in culture.

The Hep G2 cell line is derived from a human hepatic carcinoma (ref. ECACC No. 85011430).

The cells are cultured at 37° C., 5% $CO_2$ in 96-well microtitration plates at a rate of 40 000 cells (200 µl) per well in a DMEM buffer, 10% foetal calf serum, 1% Glutamax+ antibiotics, for 24 hours. The culture medium is then removed and replaced with the same medium containing the test substances at a concentration of 10 µm. The cells are incubated for 24 hours at 37° C., 5% $CO_2$ and the medium is then removed.

The amount of apolipoprotein CIII secreted into the medium is measured by means of an assay of ELISA type. Each sample of culture medium is diluted 5-fold in a 100 mM phosphate buffer, 1% BSA. 100 µl of each dilution are placed in the wells of 96-well microtitration plates sensitized beforehand with an anti(human Apo CIII) polyclonal antibody for 18 hours and passivated at a rate of 1 µg per well in 100 mM PBS and passivated with 200 µl of 100 mM PBS per 1% BSA for 1 hour at 20° C.

Each dilution of medium is incubated for 2 hours at 37° C. and the wells are then washed with 4 baths of 100 mM PBS, 0.3% Tween 20. 100 µl of a solution diluted in 100 mM PBS, 1% BSA of anti(apo CIII) polyclonal antibody coupled to peroxidase are added to each well and incubated at 37° C. for 2 hours. After a further washing identical to the previous washing, 100 µl of a 50 mM phosphate buffer, 15 mM citrate, pH=5.5 containing 1.5 mg/ml of ortho-phenylenediamine and 0.5 µl/ml of hydrogen peroxide ($H_2O_2$) are added to each well. The plate is incubated for 20 minutes in the dark and the reaction is then stopped by adding 100 µl of 1N HCl.

The optical density is read directly using a spectrophotometer at 492 nm. The amount of Apo CIII is calculated relative to a calibration curve produced using an assayed human serum of Apo CIII and diluted under the same conditions as the Apo CIII contained in the culture medium.

In the absence of a chemical treatment, the response of the cells is 100% (0% inhibition). Under the conditions used, the effect of DMSO on the cells is negligible. The toxicity of the chemical substances on the cells is measured by the technique of staining with neutral red.

The active substances bring about a reduction in the secretion of Apo CIII into the medium by the adherent cells. The concentration of Apo CIII is measured for each treatment and compared with the control test (no treatment).

The percentage of inhibition is calculated according to:

$$100 - \frac{(Apo\ CIII\ \text{concentration with treatment} \times 100)}{Apo\ CIII\ \text{concentration without treatment}}$$

The percentage of inhibition is calculated only for the substances that show no toxicity on the Hep G2 cells.

By way of example, the percentage of inhibition measured for the compound of formula I in which X=S; n=0; $R_2$=$R_3$=$R_6$=H; $R_7$=4-biphenyl and $R_4$ and $R_5$ together form —$CR_6$=$CR_7$— (Example 4 below) is 80-100 micromolar %. The concentration of compound of Example 4 which gives a 50% inhibition of the secretion of Apo CIII in this test is 17.4 µM. No cell toxicity is observed with the compound of Example 4 for the concentrations studied.

The invention is illustrated hereinbelow with the aid of preparations and examples. It is not intended to be limited to the disclosure of these specific examples.

PREPARATION 1

Preparation of the Thione of Formula IIa in which n=0; and $R_2$=$R_3$=H

The title compound is prepared by carrying out the process described in Spindler Juergen; Kempter Gerhard; Z. Chem.; 27; 1; 1987; 36-37. Its melting point is 195° C.

PREPARATION 2

Preparation of the Thione of Formula IIa in which n=0; $R_2$=—$C_6H_5$ and $R_3$=H The title compound is prepared in accordance with the teaching of FR 2 528 838.

PREPARATION 3

Preparation of the thione of formula XI in which n=0; $R_2$=$R_3$=H; $R_a$=$R_b$=—$CH_3$ (a) N-(2,2-Dimethoxyethyl)-2-(2-nitro-phenyl)acetamide 21.0 g (0.2 mol) of aminoacetaldehyde dimethyl acetal dissolved in 200 ml of chloroform are placed in a reactor together with 22.2 g (0.22 mol) of triethylamine. The reaction medium is brought to and maintained at 10° C. A solution of 0.2 mol of 2-nitrophenylacetyl chloride in 200 ml of chloroform is added to this solution. The reaction medium is allowed to return to room temperature and stirring is continued for 12 hours.

Aqueous sodium hydroxide solution is then added, after which the organic phase is allowed to separate by settling and is separated out and dried over anhydrous sodium sulphate. After evaporation of the solvent under reduced pressure, a beige-coloured solid is obtained, which is recrystallized from a mixture of hexane and ethyl acetate. 35 g of a solid with a melting point of between 89 and 90° C. are thus obtained.

(b) N-(2,2-Dimethoxyethyl)-2-(2-aminophenyl)-acetamide 40 g of the compound obtained in step (a) above dissolved in 750 ml of ethanol are hydrogenated in an autoclave in the presence of 5 g of 5% palladium-on-charcoal at a pressure of 120 bar of hydrogen.

After filtering off the catalyst and evaporating off the solvent, 35 g of an oil are obtained, which are used in crude form in the rest of the synthesis.

(c) N-(2,2-Dimethoxyethyl)-2-(2-aminophenyl)-ethylamine 28.1 g (0.74 mol) of lithium aluminium hydride suspended in 280 ml of anhydrous tetrahydrofuran are placed in a 1-liter reactor maintained under an inert atmosphere.

The reaction medium is cooled to a temperature below 10° C. and 35.3 g of the compound obtained in step (b) dissolved in 350 ml of anhydrous tetrahydrofuran are added to this solution, maintained at this temperature. The mixture is maintained at the reflux point of the solvent for 8 hours with stirring.

The reaction medium is again cooled to a temperature below 10° C. and 100 ml of water are added slowly to this solution so as to destroy the excess hydride present. The aluminium hydroxides formed are drained and rinsed with chloroform.

The organic phases separated out are dried over anhydrous sodium sulphate and then evaporated under reduced pressure. 23 g of an oil are thus isolated, and are used in crude form in the next step.

(d) 3-(2,2-Dimethoxyethyl)-4,5-dihydro-(1H,3H)-1,3-benzodiazepine-2-thione 22.6 g (0.298 mol) of carbon sulphide dissolved in 180 ml of ethanol are placed in a 500 ml reactor.

0.149 mol of the compound obtained in the preceding step dissolved in 150 ml of ethanol is added to this solution, at room temperature. The temperature rises from 18 to 22° C. The reaction medium is left stirring for 12 hours at room temperature and the reaction medium is then maintained at the reflux point of the solvent for 6 hours. The mixture is then allowed to return to room temperature, after which the solvent is evaporated off under reduced pressure. A thick green oil is obtained, which is recrystallized from 100 ml of ethanol. 21 g of a solid with a melting point of 79 to 81° C. are thus isolated.

PREPARATION 4

Preparation of the Thione of Formula XXX in which n=0; $R_2$=$R_6$=H; $R_7$=—$C_6H_5$ The title compound is prepared in accordance with the teaching of FR 2 518 544.

PREPARATION 5

Preparation of the Compound of Formula XIII in which n=0; $R_2$=$R_3$=$R_6$=H; $R_7$=—$C_6H_5$ 11.6 g (0.039 mol) of 3-(2-hydroxy-1-phenylethyl)-(1H, 3H)-1,3-benzodiazepine-2-thione suspended in 120 ml of ethanol are placed in a 250 ml reactor.

11.0 g (0.078 mol) of methyl iodide are added to this solution and the reaction medium is then maintained at the reflux point of the solvent for 1 hour. A considerable evolution of methyl mercaptan is observed.

The mixture is allowed to return to room temperature and the solvent is then evaporated off under reduced pressure. The residue is taken up in diethyl ether and dilute aqueous ammonium hydroxide solution. A white precipitate forms, which is isolated by draining. 7.6 g of a product with a melting point of 137 to 139° C. are obtained, and are recrystallized from a mixture of hexane and ethyl acetate. The product thus isolated has a melting point of 142 to 144° C.

The hydrochloride of the title compound recrystallizes from acetone and has a melting point of 132 to 135° C.

PREPARATION 6

Preparation of the Sulphide of Formula V in which n=0; $R_2$=$R_3$=H and alk=—$CH_3$ 33.2 g (0.1862 mol) of the thione obtained in Preparation 1 and 300 ml of methanol are placed in a 1 l reactor. The mixture is stirred until dissolution is complete. Next, 23.2 ml (0.3724 mol, 2 eq.) of $CH_3I$ dissolved in 50 ml of methanol are added dropwise to this mixture.

The reaction medium is maintained at reflux. After 1 hour, the solvent is evaporated off under reduced pressure and the residue is then taken up in 500 ml of diethyl ether. A precipitate forms, which is dissolved and washed three times with 50 ml of diethyl ether and then dried under reduced pressure. 59.3 g of a cream-coloured product (yield=99.4%) with a melting point of 171-173° C. are thus isolated.

$^1$H NMR (300 MHz, DMSO) δ (ppm)

11.42 (1H, s); 10.10 (1H, s); 7.45-7.24 (4H, m); 3.80-3.77 (2H, m); 3.27-3.24 (2H, m); 2.85 (3H, s).

EXAMPLE 1

Preparation of the Compound of Formula I in which X=—$NCH_3$; n=0; $R_2$=$R_3$=$R_6$=H; $R_4$+$R_5$= —$CR_6$=$CR_7$—; $R_7$=—OH 8.5 g (0.0264 mol) of the sulphide of formula V obtained in Preparation 6, 125 ml of acetonitrile dried over molecular sieves (4 Å) and 6.8 g of ethyl sarcosinate are placed in a 250 ml reactor maintained under a nitrogen atmosphere. The mixture is stirred at room temperature for 15 hours, a further 2 g of ethyl sarcosinate are then added and the reaction medium is refluxed for 6 hours. Next, a further 2 g of ethyl sarcosinate are added to the reaction medium and the mixture is refluxed for a further 14 hours. After this reaction time, no further evolution of $CH_3SH$ is observed.

The reaction medium is then concentrated by evaporation under reduced pressure, after which the beige-coloured solid obtained is taken up in 200 ml of water plus 30 ml of aqueous 7% sodium bicarbonate solution. The solution is extracted with dichloromethane and dried over anhydrous sodium sulphate, and the solvents are then evaporated off. The residue is then purified by chromatography on silica gel, using a 4/1 dichloromethane/ethyl acetate mixture. 3.4 g of a yellow solid with a melting point of 132-134° C. are thus isolated. After recrystallization from a mixture of 30 ml of hexane and 40 ml of ethyl acetate, 2.7 g of a pale yellow solid (yield=47.5%) with a melting point of 132-134° C. are isolated.

$^1$H NMR (300 MHz, DMSO) δ (ppm):

7.30-7.27 (1H, m); 7.22-7.16 (2H, m); 7.05-6.99 (1H, m); 4.18 (2H, s); 3.88 (2H, s); 3.14 (3H, s); 3.12-3.07 (2H, s).

EXAMPLE 2

Preparation of the Compound of Formula I in which X=—NH; n=0; $R_2$=$R_3$=$R_6$=H; $R_4$+$R_5$= —$CR_6$=$CR_7$—; $R_7$=—$C_6H_5$ a) Preparation of the compound of formula VII in which $R_6$=$R_2$=$R_3$=H; n=0; $R_7$=—$C_6H_5$; $R_a$ and $R_b$ together form —$CH_2$—$CH_2$—

4.4 g (0.01381 mol) of the sulphide obtained in Preparation 6, 80 ml of acetonitrile and 5.2 g (0.029 mol; 2.1 eq.) of the following amine:

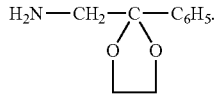

are placed in a 100 ml reactor maintained under a nitrogen atmosphere.

The reaction medium is maintained at 50° C. for 12 hours and is then allowed to return to room temperature (20° C.). 100 ml of diethyl ether are then added. The precipitate formed is filtered off at 20° C. and washed 3 times with 15 ml of diethyl ether and then dried under reduced pressure. 5.5 g of a cream-coloured solid product with a melting point of 220° C. are thus obtained. The residue is taken up in aqueous 7% sodium bicarbonate solution (100 ml) and left stirring for 30 minutes and then filtered, washed with water and dried under reduced pressure.

4.5 g of a cream-coloured solid with a melting point of 217-219° C. are thus obtained. After recrystallization from 100 ml of ethanol, 4.3 g of a white solid with a melting point of 217-219° C. are isolated. This compound is the hydriodide salt of the title compound, as results from the elemental analysis of the product obtained (yield=69%).

$^1$H NMR (300 MHz, DMSO) δ (ppm):

9.39 (s, 1H); 8.36 (1H, s); 7.32-7.00 (7H, m); 6.87 (2H, t, J=7 Hz); 3.9-3.88 (2H, m); 3.62-3.60 (2H, m); 3.4.8 (2H, s); 3.26 (2H, t, J=4.5 Hz); 2.80 (2H, t, J=4.6. Hz).

b) Preparation of the compound of formula I in which X=NH; n=0; $R_2$=$R_3$=$R_6$=H; $R_4$+$R_5$=—$CR_6$=$CR_7$—; $R_7$=—$C_6H_5$ 3 g of the compound obtained in step a) above (0.009277 mol), 200 ml of ethanol and 200 ml of 5N HCl are placed in a 500 ml reactor maintained under a nitrogen atmosphere. The mixture is refluxed for 5 hours and the solvent is then evaporated off under reduced pressure. 200 ml of water are added to the residue and the mixture is washed twice with 150 ml of diethyl ether. The solution is basified with aqueous 30% sodium hydroxide solution, while keeping the temperature below 20° C. The cream-coloured precipitate formed is filtered off and then washed with water and dried under reduced pressure at 80° C. 1.8 g (yield=73.8%) of a cream-coloured solid with a melting point of 194-206° C. are thus isolated.

$^1$H NMR (300 MHz, DMSO) δ (ppm)

9.18 (1H, s); 7.28-7.11 (8H, m); 6.67-6.65 (1H, m); 6.55 (1H, s); 3.94 (2H, t, J=4.7 Hz); 2.91 (2H, t, J=4.6 Hz).

EXAMPLE 3

Preparation of the Compound of Formula I in which X=$NCH_3$; n=0; $R_2$=$R_3$=$R_6$=H; $R_4$+$R_5$= —$CR_6$=$CR_7$; $R_7$=—$C_6H_5$ 1.4 g (0.00531 mol) of the compound obtained in Example 2 and 46 ml of dimethylformamide dried over molecular sieves (4 Å) are placed in a 100 ml reactor. The mixture is stirred until completely dissolved. 0.22 g of a 60% dispersion of sodium hydride in oil (0.005575; 1.05 eq.) is then added, and the mixture is left to react, with stirring, for 30 minutes. Next, 0.4 ml (0.006372; 1.2 eq.) of methyl iodide is added in a single portion. The reaction medium is stirred for 48 hours and is then poured into 600 ml of water and the solution is extracted with dichloromethane. The combined extracts are washed with water and dried over anhydrous sodium sulphate, and the solvent is evaporated off under reduced pressure. 1.1 g of a yellow oil are obtained. The maleate salt of this compound is prepared by the action of one equivalent of maleic acid in methanol at room temperature. The solvent is evaporated off and the residue is recrystallized from methanol. 0.78 g (yield=37.5%) of a white solid with a melting point of 173-175° C. is thus isolated.

$^1$H NMR (300 MHz, DMSO) δ (ppm):

7.51-7.23 (10H, m); 6.10 (2H, s); 4.11-4.08 (2H, m); 3.54 (3H, s); 3.19 (2H, t, J=5.1 Hz).

EXAMPLE 4

Preparation of a Compound of Formula I in which X=S; n=0; $R_2$=$R_3$=$R_6$=H; $R_7$=p-(phenyl)phenyl; $R_4$ and $R_5$ together form —$CR_6$=$CR_7$—

16.5 g (92.5 mmol) of the thione obtained in Preparation 1, 390 ml of glacial acetic acid and 25.5 g (92.5 mmol) of bromomethyl para-phenylphenyl ketone are introduced into a 500 ml reactor equipped with a condenser. The mixture is gradually brought to reflux, with stirring, and maintained at reflux for 3 hours. The reaction medium is then cooled to 15° C. The precipitate (hydrobromide) is filtered off, rinsed with diethyl ether and dried. The residue is taken up in 200 ml of ice-cold water and the resulting solution is basified slowly by addition of aqueous 30% sodium hydroxide solution with vigorous stirring. The amount of sodium hydroxide required to observe the stability of alkaline pH is thus added. The solution is then extracted twice with methylene chloride. Next, the extracts are rinsed with water and dried over anhydrous sodium sulphate and the solvent is then evaporated off under reduced pressure. A pale yellow solid is thus isolated (yield=85%) which is recrystallized from toluene so as to obtain the title compound, in pure form, which has a melting point of 199.5-200° C. (Example 4).

The hydrochloride salt of this compound is prepared by adding a 33% solution of hydrogen chloride in ethanol. The melting point of this salt is 299.5-300° C. (Example 44).

$^1$H NMR (300 MHz, DMSO-d6):

3.02 (2H, m); 3.97 (2H, m); 6.4 (1H, s); 6.8 (1H, m); 7 (2H, m); 7.1 (1H, m); 7.4-7.6 (5H, m); 7.7-7.9 (4H, m).

$^1$H NMR (300 MHz, DMSO-d6) of the hydrochloride:

3 (2H, m); 4 (2H, m); 6.8-7.7 (14H); 13 (1H, exchangeable s).

EXAMPLE 5

Preparation of a Compound of Formula I in which X=S; n=0; $R_4$=$R_2$=$R_3$=H; $R_5$=$CH_2$—CO-(p-phenylphenyl)

2.7 g (15 mmol) of the thione obtained in Preparation 1 and 150 ml of tetrahydrofuran are placed in a 250 ml three-necked flask equipped with a condenser with $CaCl_2$ guard tube.

The reaction medium is heated gently until the thione has completely dissolved, followed by slow addition of 6.6 g (24 mmol; 1.6 equivalents) of bromomethyl para-phenylphenyl ketone in 50 ml of tetrahydrofuran. A product which precipitates is observed. The reaction medium is kept stirring for 1 hour 30 minutes. Next, the precipitate is filtered off and rinsed with diethyl ether. The precipitate is then suspended in 200 ml of ice-cold water and the suspension is then basified slowly by adding aqueous 33% sodium hydroxide solution with vigorous stirring. The amount of sodium hydroxide added is the amount required to obtain stability of the alkaline pH. The white solid is then filtered off and recrystallized from ethanol. The title compound, which has a melting point of 239.5-240° C. (yield=68%), is thus isolated.

$^1$H NMR (300 MHz, DMSO-6) δ (ppm): 3 (2H, m) 3.2 (1H, m); 3.4 (1H, m); 3.5 (1H, d, J=11.8 Hz); 3.7 (1H, d, J=11.8 Hz); 6.9-7.9 (13H, m).

EXAMPLE 6

Preparation of a Compound of Formula I in which x=S; n=0; $R_4$ and $R_5$ together form —$CR_6$=$CR_7$—; $R_2$=—$C_6H_5$; $R_3$=H; $R_6$=H; $R_7$=—OH 10. g (0.039 mol) of the thione obtained in Preparation 2 are placed in a 250 ml reactor containing 125 ml of acetic acid. 7.9 g (0.047 mol) of ethyl bromoacetate are added dropwise to this solution and the reaction medium is refluxed for 9 hours. A white precipitate is formed. After cooling to room temperature, the hydrobromide formed is drained off. The product is dried and is suspended in water. 30% ammonium hydroxide solution is added to this suspension until the pH is basic. The product is drained and then dried, after which it is recrystallized from a mixture of hexane and ethyl acetate. 8.2 g of the title compound, which has a melting point of 156-158° C., are thus isolated.

EXAMPLE 7

Preparation of a Compound of Formula I in which X=S; n=0; $R_4$ and $R_5$ together form —$CR_6$=$CR_7$—; $R_2$=$R_3$=$R_6$=H; $R_7$=OH 3.0 g (0.0168 mol) of 2-thione-4,5-dihydro-1,3-benzodiazepine and 3.75 ml (0.0336 mol) of ethyl bromoacetate in 50 ml of toluene are placed in a 250 ml three-necked flask.

The reaction mixture is then refluxed for 1 hour with stirring. The mixture is allowed to return to room temperature, water and aqueous ammonium hydroxide solution are then added and the reaction medium is extracted with ethyl acetate. After drying the various organic extracts over anhydrous sodium sulphate, the reaction medium is evaporated. 1.4 g of an ochre-coloured solid which recrystallizes from ethanol are thus isolated. After recrystallization, the melting point of this solid is 111 to 112° C.

$^1$H NMR (300 MHz, CDCl$_3$) δ (ppm): 3.23-3.25 (2H, m); 4.18 (4H, s); 7.26-7.3 (2H, m); 7.43-7.5 (2H, m).

EXAMPLE 8

Preparation of a Compound of Formula I in which x=S; n=0; $R_4$ and $R_5$ together form —$CR_6$=$CR_7$—; $R_2$=$R_3$=$R_6$=$R_7$=H 14.0 g of the compound obtained in Preparation 3 in 140 ml of aqueous 50% sulphuric acid solution are placed in a 250 ml reactor. The mixture is maintained for 2 hours at the reflux point of the solvent. The reaction medium is allowed to return to room temperature and is then poured onto a mixture of water and ice. After extraction with chloroform and drying of the extracts over anhydrous sodium sulphate, the solvent is evaporated off. 9 g of a thick oil are thus obtained. This oil is dissolved in 100 ml of acetone. 5.7 g of maleic acid are then added. The product obtained after concentrating the solution is the maleate of the title compound. This product is recrystallized from acetone. The product obtained has a melting point of between 121 and 123° C.

The compounds of Examples 9 to 192 below were obtained using the processes illustrated in Examples 1 to 8 above.

Tables 1 to 6 below report the characterization data obtained for each of these compounds.

m.p. denotes the melting point.

The NMR spectra were recorded at 300 MHz in solvent S.

The abbreviations s, d, t and m have the following meanings:
s: singlet
d: doublet
t: triplet
m: multiplet.

TABLE 1

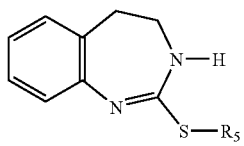

| Example | $R_5$ | m.p. (° C.) | $^1$H NMR δ(ppm) |
|---|---|---|---|
| 9 | CH$_2$—CO—$^t$Bu | 200-200.5 | S = CDCl$_3$<br>1.2(9H, s); 3.2(2H, m); 7(1H, d, J=7.5 Hz); 7.1(1H, t, J=7.5 Hz); 7.3(1H, t, J=7.5 Hz); 7.5(1H exchangeable, s); 7.8(1H, d, J=7.5 Hz). |
| 10 | CH$_2$—CO—CO—Oet | 174-175 | S = DMSO-d6<br>1.2(3H, t, J=7.1 Hz); 3.2(2H, m); 3.7(2H, m); 3.7(1H, d, J=12.3 Hz); 4.0(1H, d, J=12.3 Hz); 4.2(2H, m, J=7.1 Hz); 7.3(4H, m); 8.7(1H exchangeable, s); 12.3(1H exchangeable, s). |
| 11, HBr | —CH$_2$\[geranyl group\] | 119-119.5 | S = DMSO-d6<br>1.5-1.7(9H, m); 3.1(2H, m); 3.6(2H, m); 4(2H); 5(1H); 5.3(1H); 7.1-7.4(4H, m); 10.5(1H exchangeable, s); 11.5(1H exchangeable, s). |
| 12 | CH$_2$—CO—(2-pyridyl) | 194-195 | S = DMSO-d6<br>3(2H, m); 3.3(1H, m); 3.6(1H, m); 3.8(1H, d, J=12.2 Hz); 4(1H, d, J=12.2 Hz). |

TABLE 1-continued

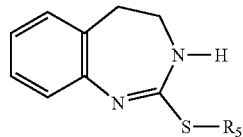

| Example | R$_5$ | m.p. (° C.) | $^1$H NMR δ(ppm) |
|---|---|---|---|
| 13 | CH$_2$—CO—(3-pyridyl) | 200-200.5 | S = DMSO-d6<br>2.9(2H, m); 3.1(1H, m); 3.3(1H, m); 3.4(1H, d, J=11.8 Hz); 3.6(1H, d, J=11.8 Hz); 6.8(1H, m); 6.9(2H, m); 7.1(1H, m); 7.4(1H exchangeable, s); 7.5(1H, m); 7.9(1H, m); 8.6(1H, m); 8.8(1H, m). |
| 14 | CH$_2$—CO—(2-furyl) | 158-158.5 | S = DMSO-d6<br>3(2H, m); 3.3(2H, m); 3.5(1H, d, J=11.8 Hz); 3.9(1H, d, J=11.8 Hz); 6.6-6.8(2H, 2m); 7(1H, t, J=1.5 Hz); 7.1(2H, d); 7.25(1H, t); 7.5(1H, s); 7.9(1H, s). |
| 15 | CH$_2$—CO—(4-pyridyl) | 217.2-217.4 | S = DMSO-d6<br>2.9(2H, m); 3.1(1H, m); 3.3(1H, m); 3.4(1H, d, J=12.1 Hz); 3.5(1H, d, J=12.1 Hz); 7.5(1H exchangeable, s); 6.8-7.2(4H, m); 7.5(2H, d, J=6 Hz); 8.6(2H, d, J=6 Hz). |
| 16 | —CH$_2$—C(=CH$_2$)—C$_6$H$_5$ | 209.8-210 | S = DMSO-d6<br>3.1(2H, m); 3.6(2H, m); 4.5(2H, s); 5.5(1H, s); 5.6(1H, s); 7.2-7.5(9H, m); 10.5(1H exchangeable, s); 11.4(1H exchangeable, s); |
| 17 | CH$_2$—C$_6$H$_5$ | 187.5-188 | S = DMSO-d6<br>4.8(2H, s); 3(2H, m); 3.6(2H, m); 7.1-7.5(m). |
| 18 | —CH$_2$—CH=C(CH$_3$)$_2$ | 159.7-160 | S = DMSO-d6<br>1.5(6H); 3(2H); 3.5(2H); 3.9(2H); 5.1(1H); 7.4(4H); 10.8(1H exchangeable); 11.5(1H). |
| 19 | CH$_2$—CO—(2,3-dihydrobenzofuran-5-yl) | 187-187.5 | S = DMSO-d6<br>2.7-3.4(8H, m); 4.4(2H, m); 6.6-7.3(7H, m) |
| 20 | CH$_2$—CO—(2-furyl) | 199-199.2 | S = DMSO-d6<br>3.8(1H, d, J=12.3 Hz); 4.0(1H, d, J=12.3 Hz); 3-3.7(4H, m); 6.5-7.8(7H, m); 8.7(1H exchangeable, s); 13(1H exchangeable, s). |
| 21 | —CH$_2$—CO—C$_6$H$_5$ | 210° C. | S = DMSO-d6<br>2.7-2.8(2H, m); 2.8-2.9(1H, m); 3.1-3.2(1H, m); 3.3(1H, d, J=12 Hz); 3.4(1H, d, J=12 Hz); 6.7-7.0(5H, m); 7.2-7.4(4H, m). |
| 22 | —CH$_2$—CO—CH$_3$ | 184-186 | S = DMSO-d6<br>1.4(3H, s); 2.9(2H, m); 3.2(1H, d, J=11 Hz); 3.3(1H, d, J=11 Hz); 3.3-3.5(2H, m); 6.5(1H, s); 6.8-7.1(4H, m). |
| 23 | —CH$_2$—CH$_2$—CH$_3$ | 152-154 | S = DMSO-d6<br>0.9(3H, t, J=7 Hz); 1.5-1.6(2H, m); 3.0-3.1(2H, m); 3.3(2H, t, J=7 Hz); 3.5-3.6(2H, m); 7.0-7.1(1H, m); 7.2-7.3(2H, m); 7.3-7.4(1H, m). |
| 24 | —CH$_2$—CO—(CH$_2$)$_7$—CH$_3$ | 134-136 | S = CDCl$_3$<br>0.8(3H, t, J=7 Hz); 1.2-1.4(12H, m); 1.7-1.8(2H, m); 2.8-3.0(3H, m); 3.3-3.4(2H, m); 3.6-3.7(1H, m); 4.0(1H, s, proton exchangeable with D$_2$O); 6.8-6.9(2H, m); 7.0-7.1(2H, m). |
| 25 | —(CH$_2$)$_7$—CH$_3$ | 150-152 | S = DMSO-d6<br>0.7-0.9(3H, m); 1.1-1.3(10H, m); 1.4-1.6(2H, m); 2.5-2.6(2H, m); 3.1-3.2(2H, m); 4.2-4.3(2H, m); 6.8(1H, s); 7.0-7.1(1H, m); 7.1-7.4(3H, m). |
| 26 | —CH$_2$—CO—CH$_2$—C$_6$H$_5$ | 185-187 | S = DMSO-d6<br>2.8-2.9(5H, m); 3.2(1H, d, J=12 Hz); 3.3-3.4(1H, m); 3.5-3.6(1H, m); 6.5(1H, s, exchangeable with CF$_3$COOD); 6.7-6.9(4H, m); 7.1-7.2(5H, m). |
| 27 | —CH$_2$—C(CH$_3$)=CH$_2$ | 170-172 | S = DMSO-d6<br>1.6(3H, s); 2.8-2.9(2H, m); 3.4-3.5(2H, m); 3.9(2H, s); 4.7(1H, s); 4.8(1H, s); 6.9-7.1(3H, m); 7.3-7.4(1H, m). |

TABLE 1-continued

[Structure: benzo-fused 7-membered ring with N—H and N=C-S-R5]

| Example | R5 | m.p. (° C.) | ¹H NMR δ(ppm) |
|---|---|---|---|
| 28 | —CH2-(3,5-dimethylisoxazol-4-yl) | 121-123 | S = DMSO-d6<br>2.5(3H, s); 2.6(3H, s); 3.2-3.3(2H, m); 3.6(2H, s, exchangeable with CF3CO2D); 3.8-3.9(2H, m); 4.8(2H, s); 7.4-7.6(3H, m); 7.7-7.8(1H, m). |
| 29 | CH2—CO—(3,4-dihydroxyphenyl) | 180-185 | S = DMSO-d6<br>2.85-3.66(6H, m);<br>6.77-7.26(8H, m); 9.06(2H, s; exchangeable CF3COOD). |
| 30 | —CH2-(cyclohex-1-en-1-yl) | 74-76 | S = CDCl3<br>1.6-1.4(4H, m); 2.0-1.9(4H, m); 3.0-2.9(2H, m); 3.7-3.5(4H, m); 5.0(1H, s, exchangeable D2O); 5.6(1H, s); 7.1-6.8(4H, m). |

The following three compounds in Table 2 moreover illustrate the preparation of compounds of formula I in which X=S, R4=H, R3=H.

TABLE 2

[Structure: (R1)n-substituted benzo-fused 7-membered ring with R2, NH, N=C-SR5]

| Ex | n/R1 | R2 | R5 | m.p. (° C.) | ¹H NMR δ(ppm) |
|---|---|---|---|---|---|
| 31 | 0/— | 3-chlorophenyl | CH2—CO—(4-biphenylyl) | 202-204 | S = DMSO-d6<br>3.4-3.2(4H, m); 4.4-4.3(1H, m); 7.9-6.7(17H, m). |
| 32 | 0/— | $C_6H_5$ | CH2—CH2—OH | 181-185 | |
| 33 | 1/7-Cl | H | CH2—CO—(4-biphenylyl) | 190-192 | S = DMSO-d6<br>2.75(m, 2H); 2.9-3.0(m, 1H); 3.1-3.2(m, 1H); 3.3(d, J=12 Hz, 1H); 3.4(d, J=12 Hz, 1H); 6.9-6.8(m, 2H); 7.1-7.0(m, 1H); 7.6-7.2(m, 9H). |

TABLE 3

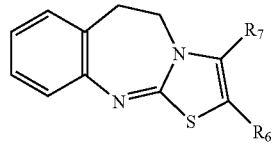

| Ex | R₆ | R₇ | m.p. (° C.) | ¹H NMR: δ(ppm) |
|---|---|---|---|---|
| 34 | —CH₃ | C₆H₅ | 112-113 | S = DMSO-d6<br>2.1(3H, s); 3.1(2H, m); 3.9(2H, m);7-7.3(4H, m); 7.6-7.7(5H, m). |
| 35 | —H | —CO—Oet | 140-150 | S = DMSO-d6<br>1.5(3H, t, J=7.1 Hz); 3.5(2H, m); 4.5(2H, d, 7.1 Hz); 4.9(2H, m); 7.3-7.6(4H, m);<br>8.2(1H, s). |
| 36 | —H | 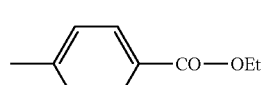 —CO—OEt | 231-233 | S = DMSO-d6<br>1.3(3H, t, J=7.1 Hz); 4.3(2H, d, J=7.1 Hz); 3.3(2H, m); 4.2(2H, m); 7.2-7.4(5H, m); 7.7(2H, d, J=8.2 Hz); 8.1(2H, d, J=8.2 Hz). |
| 37 | —H | -ᵗBu | 112.3 | S = DMSO-d6<br>1.26(9H, s); 3.1(2H, m); 4.1(2H, m); 1.95(1H, s); 6.7-7(4H, m). |
| 38 | —H | 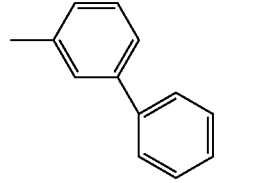 | 138-139 | S = DMSO-d6<br>3(2H, m); 4(2H, m);<br>6.5(1H, s); 6.8(1H, t, J=7.3 Hz);<br>6.9(2H, m); 7.1(1H, t, J=7.3 Hz); 7.4-7.6(5H, m); 7.7(4H, m). |
| 39 | —H | 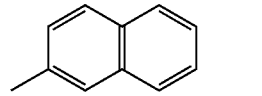 | 188.5-189.5 | S = DMSO-d6<br>6.6(1H, s); 6.9-7.3(4H, m); 7.7(3H, m);<br>8.1(4H, m); 3.1(2H, m); 4.1(2H, m). |
| 40 | H | 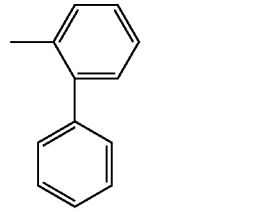 | 198.5-199 | S = CDCl₃<br>2(1H, m); 2.6(1H, m); 3.4(2H, m); 6(1H, s);<br>6.7(2H, m); 7.1(2H, m); 7.3-7.6(9H, m). |
| 41 | —H | 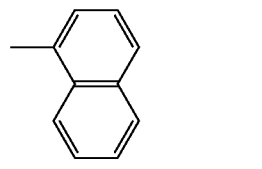 | 209.3 | S = DMSO-d6<br>2.9(2H, m); 3.5(2H, m); 6.4(1H, s); 6.7(1H, m);<br>6.8(1H, m); 7(1H, m); 7.1(1H, m); 7.6(4H, m); 7.7(1H, m); 8(2H, m). |
| 42 | —C₆H₅ | H | 199.5-200 | S = DMSO-d6<br>3(2H, m); 4(2H, m); 6.8-7.3(10H, m). |
| 43 | —H | 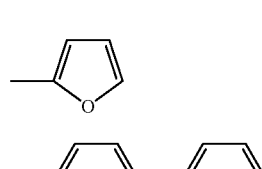 | 157-158 | S = DMSO-d6<br>3.1(2H, m); 4.2(2H, m); 6.5(1H); 6.8(1H, s);<br>6.9-7.3(5H, m); 7.7(4H, s); 13.5(1H exchangeable, s). |
| 44 HCl | —H | 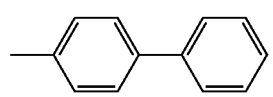 | 299.5-300 | — |
| 45 | —CH₂—COOH | —C₆H₅ | 216 | — |
| 46 | —H | —C₆H₅ | 223-231 | S = DMSO-d6<br>3.4-3.5(2H, m); 4.3-4.4(2H, m); 7.3-7.5(4H, m); 7.6-7.7(6H, m);<br>14(1H, s, exchangeable with CF₃COOD). |
| 47 | —H | 2-naphthyl | 188.5-189.5 | — |

TABLE 3-continued

| Ex | R$_6$ | R$_7$ | m.p. (° C.) | $^1$H NMR: δ(ppm) |
|---|---|---|---|---|
| 48 | —CH$_3$ | —C$_6$H$_5$ | 112-113 | |
| 49 | —H | 4-Cl-C$_6$H$_4$— | 154° C. | S = CDCl$_3$<br>3.04-3.08(2H, m); 3.9-3.93(2H, m); 5.94(1H, s); 6.9-6.95(2H, m); 7.18-7.29(4H, m); 7.41-7.44(2H, m). |
| 50 | —H | —CH$_3$ | 194-196 | S = DMSO-d6<br>0.7(3H, s); 3.3-3.4(2H, m); 4.3-4.4(2H, m); 7.0(1H, s); 7.1-7.2(1H, m); 7.3-7.4(2H, m); 7.50-7.55(1H, m). |
| 51 | —H | —CH$_2$—C$_6$H$_5$ | 130-132 | S = CDCl$_3$<br>2.8-2.9(2H, m); 3.7(2H, m); 3.7-3.5(2H, m); 5.6(1H, s); 6.7-6.8(2H, m); 7.0-7.3(7H, m). |
| 52 | —H | 4-Br-C$_6$H$_4$— | 154° C. | S = CDCl$_3$<br>3.26-3.29(2H, m); 4.12-4.15(2H, m); 6.15(1H, s); 7.11-7.18(2H, m); 7.36-7.5(4H, m); 7.78-7.8(2H, m). |
| 53 | —H | 4-(4-CH$_3$O-C$_6$H$_4$)-C$_6$H$_4$— | 189° C. | S = CDCl$_3$<br>3.04-3.07(2H, m); 3.85(3H, s); 3.96-4(2H, m); 5.92(1H, s); 6.86-7.6(12H, m). |
| 54 | —H | 4-(4-Cl-C$_6$H$_4$)-C$_6$H$_4$— | 226-228 | S = DMSO-d6<br>3.0(2H, m); 3.9(2H, m); 6.4(1H, s); 6.8-7.0(4H, m); 7.5-7.6(4H, m); 7.7-7.8(4H, m). |
| 55 | —H | 4-(4-CF$_3$-C$_6$H$_4$)-C$_6$H$_4$— | 201° C. | S = CDCl$_3$<br>2.88-2.91(2H, m); 3.79-3.82(2H, m); 5.79(1H, s); 6.68-6.77(2H, m); 6.96-7.02(2H, m); 7.07-7.26(2H, m); 7.46-7.56(6H, m). |
| 56 | —H | 4-(4-CH$_3$-C$_6$H$_4$)-C$_6$H$_4$— | 213 | S = CDCl$_3$<br>2.58(3H, s); 3.24(2H, t; J=4.6 Hz); 4.16(2H, t; J=4.6 Hz); 6.11(1H, s); 7.02-7.12(2H, m); 7.31-7.81(10H, m). |
| 57 | —H | 4-(3-Cl-C$_6$H$_4$)-C$_6$H$_4$— | 174-175 | S = CDCl$_3$<br>3.23(2H, q; J=2.33 Hz)<br>4.14(2H, q; J=2.33 Hz); 6.14(1H, s); 7.07-7.09(2H, m); 7.34-7.79(10H, m). |
| 58 | —H | 4-(2,3-dihydrobenzofuran-7-yl)-C$_6$H$_4$— | 173 | S = CDCl$_3$<br>3.08(2H, t; J=4.6 Hz); 3.32(2H, t; J=8.75 Hz); 4.02(2H, t; J=4.6 Hz); 4.67(2H, t; J=8.78 Hz); 5.96(1H, s); 6.88-7.01(3H, m); 7.2-7.4(6H, m); 7.77-7.86(2H, m). |
| 59 | —H | 3,4-(OH)$_2$-C$_6$H$_3$— | 183-185 | S = DMSO-d6<br>3.11-3.12(2H, m); 3.98-4.01(2H, m); 6.28(1H, s); 6.81-7.23(7H, m); 9.4(2H, s; exchangeable CF$_3$COOD). |
| 60 | —H | 4-(4-tBu-C$_6$H$_4$)-C$_6$H$_4$— | 176 | S = CDCl$_3$<br>1.52(9H, s); 3.21(2H, q; J=2.3 Hz); 4.14(2H, q; J=2.3 Hz); 6.09(1H, s); 7-7.07(2H, m); 7.32-7.8(10H, m). |

TABLE 3-continued

| Ex | R$_6$ | R$_7$ | m.p. (° C.) | $^1$H NMR: δ(ppm) |
|---|---|---|---|---|
| 61 | —H | (4'-(3-nitro)biphenyl) | 120-123 | S = CDCl$_3$<br>3.15(2H, t; J=4.65 Hz); 4.07(2H, t; J=4.65 Hz); 6.08(1H, s); 6.96-8.54(12H, m). |

Table 4 below also illustrates the preparation of compounds corresponding to the following formula:

TABLE 4

| Ex | n/R$_1$ | R$_6$ | R$_7$ | m.p. (° C.) | $^1$H NMR: δ(ppm) |
|---|---|---|---|---|---|
| 62 | 0/— | CH$_2$—CO—OEt | —C$_6$H$_5$ | 192-193 | — |
| 63 | 0/— | —H | —CH$_2$—CH$_2$—NEt$_2$ | 104-106 | — |
| 64 | 0/— |  | (2-chlorobenzyl-piperazinyl-methyl) | 223-225 | — |
| 65 | 0/— |  | (piperazinyl) | 299-301 | — |
| 66 | 1/7-Cl | —H | (4'-biphenyl) | 190-192 | S = CDCl$_3$<br>3.0-2.9(2H, m);<br>3.9-3.8(2H, m);<br>5.9(1H, s); 6.8(1H, m);<br>7.1-6.9(2H, m); 7.6-7.3(9H, m). |

EXAMPLE 66

Using the processes illustrated in the preceding examples, the compound of formula:

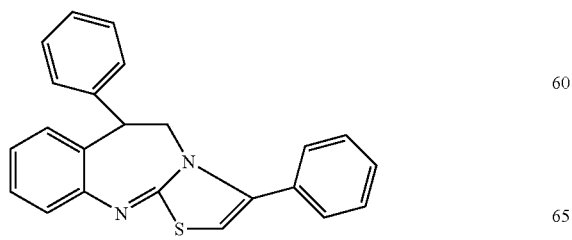

which has a melting point of 184-185° C., is prepared.

The invention also relates to pharmaceutical compositions containing an effective amount of at least one compound of formula I as defined above in combination with at least one pharmaceutically acceptable vehicle.

According to another of its aspects, the invention relates to the use of a compound of formula I as defined above for the preparation of a medicinal product for preventing or treating dyslipidaemia, atherosclerosis and diabetes or its complications.

TABLE 5

| Example | $R_2$ | $R_7$ | $R_6$ | Characterization data |
|---|---|---|---|---|
| 67 | H | 4-phenoxyphenyl | H | m.p. = 204-205° C.<br>NMR 300 MHz (DMSO): 3.2(2H, m); 4.1(2H, m); 6.3(1H, s); 6.8-6.9(2H, m); 6.9-7.0(2H, m); 7.1-7.2(4H, m); 7.2-7.3(1H, m); 7.4-7.5(4H, m)<br>MS: 371.3 (ES+) |
| 68, HCl | H | 4-(p-chlorobenzoyl)phenyl | H | m.p. = 253-255° C.<br>NMR 300 MHz (DMSO): 3.2(2H, m); 4.2(2H, m); 7.1-7.5(5H, m); 7.68(2H, d, J=8.7 Hz); 7.73(2H, d, J=8.7 Hz); 7.81(2H, d, J=8.7 Hz); 7.89(2H, d, J=8.7 Hz); 12.9(1H, s)<br>MS: 417.3 (ES+) |
| 69, HCl | H | 3,4-ethylenedioxyphenyl | H | NMR 300 MHz (DMSO): 3.2-3.3(2H, m); 4.1-4.2(2H, m); 4.3(4H, s); 6.9-7.0(3H, m); 7.1-7.2(2H, m); 7.2-7.3(1H, m); 7.3-7.4(2H, m); 13.0(1H, s)<br>MS: 337.3 (ES+) |
| 70, HCl | H | 4-cyanophenyl | H | MS: 304 (ES+) |
| 71, HCl | H | 3,4-methylenedioxyphenyl | H | MS: 322.8 (ES+) |
| 72, HCl | H | dibenzofuranyl | H | MS: 368.8 (ES+) |
| 73, HCl | H | 6-methoxynaphthalenyl | H | MS: 358.8 (ES+) |
| 74, HCl | H | 3,4,5-trimethoxyphenyl | H | MS: 369 (ES+) |
| 75, HCl | H | fluorenyl | H | MS: 367 (ES+) |
| 76, HCl | H | bromodibenzofuranyl | H | MS: 447 and 449 (ES+) |
| 77, HCl | H | 4-methyl-benzyl-cyclopentyl-NH-SO$_2$-C$_6$H$_5$ | H | MS: 516 (ES+) |
| 78, HCl | H | 3-cyanophenyl | H | MS: 304 (ES+) |

TABLE 5-continued

| Example | R$_2$ | R$_7$ | R$_6$ | Characterization data |
|---|---|---|---|---|
| 79, HCl | H | benzothien-3-yl | H | MS: 335 (ES+) |
| 80, HCl | H | 8-methyl-2-phenyl-4H-chromen-4-one (attached via chromene) | H | MS: 440.8 (ES+) (+H$_2$O); 438.8 (ES−) (+H$_2$O) |
| 81, HCl | H | 4-chlorophenylsulfonamido-methyl-(1-(p-tolyl)cyclopentyl) group | H | MS: 550, 551, 552 and 553 (ES+) |
| 82, HCl | H | 4-chlorophenylsulfonamido-methyl-(1-(p-tolyl)cyclobutyl) group | H | MS: 536, 537, 538 and 539 (ES+); 534, 535, 536 and 537 (ES−) |
| 83, HCl | H | 1-(4-methylbenzyl)cycloheptanecarbonitrile group | H | MS: 414 (ES+) |
| 84, HCl | H | 4-carboxymethyl | H | MS: 337 (ES+) |
| 85, HCl | H | 1-methylanthracen-2-yl | H | MS: 379 (ES+) |

TABLE 5-continued

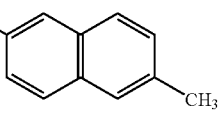

| Example | R₂ | R₇ | R₆ | Characterization data |
|---|---|---|---|---|
| 86, HCl | H | 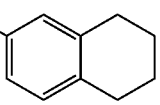 | H | MS: 343.2 (ES+) |
| 87, HCl | H | 4-methylthiophenyl | H | MS: 325.2 (ES+) |
| 88, HCl | H | 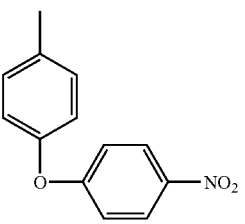 | H | MS: 333.2 (ES+) |
| 89, HCl | H | 3-(phenylsulphonyl)phenyl | H | MS: 419.2 (ES+) |
| 90, HCl | H | 2-trifluoromethoxyphenyl | H | MS: 363.1 (ES+) |
| 91, HCl | H | 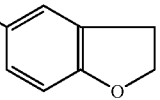 | H | MS: 416.2 (ES+) |
| 92, HCl | H | 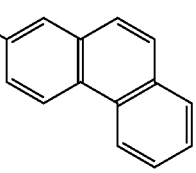 | H | MS: 321.2 (ES+) |
| 93, HCl | H | 4-(hydroxyethoxy)phenyl | H | MS: 339.1 (ES+) |
| 94, HCl | H | 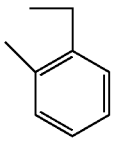 | H | MS: 379.2 (ES+) |
| 95, HCl | H | 3-nitro-4-phenylthiophenyl | H | MS: 432.1 (ES+) |
| 96, HCl | H | the SP₃ carbon atom being linked to CS R₆ + R₇ = | H | MS: 291.1 (ES+) |
| 97, HCl | H | 4-(difluoromethoxy)phenyl | H | F=278.5-279° C. NMR 300 MHz (CDCl3): 3.1-3.3(2H, m); 4.1-4.3(2H, m); 6.7(1H, t, J=72.6 Hz); 7.1-7.6(8H, m); 8.1(1H, d, J=8.7 Hz); 14.7(1H, s) MS: 345.1 (ES+) |
| 98, HCl | H | 3-methylbenzothien-2-yl | H | MS: 349.1 (ES+) |

TABLE 5-continued
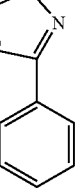
| Example | R₂ | R₇ | R₆ | Characterization data |
|---|---|---|---|---|
| 99, HCl | H | 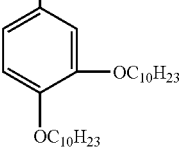 | H | MS: 346.1 (ES+) |
| 100 | H | 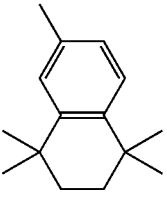 | H | MS: 591.4 (ES+) |
| 101, HCl | H | 4-phenylsulphonyl)phenyl | H | MS: 419.1 (ES+) |
| 102 | H | 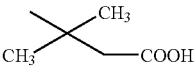 | H | MS: 389.2 (ES+) |
| 103, HCl | H | 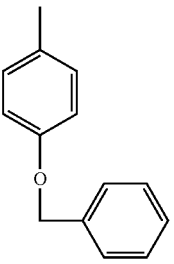 | H | MS: 303.1 (ES+) |
| 104 | H | 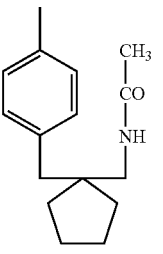 | H | MS: 383.4 (ES−) |
| 105 | H |  | H | MS: 432.5 (ES+) |
| 106 | H | 4-(diethylamino)phenyl | H | MS: 350.4 (ES+) |

TABLE 5-continued

| Example | R₂ | R₇ | R₆ | Characterization data |
|---|---|---|---|---|
| 107 | H | phenyl | 4-chlorophenyl | MS: 389 (ES+) |
| 108 | H | 4-morpholinophenyl | H | MS: 364.4 (ES+) |
| 109 | H | 3-methoxy-2,4-dimethyl-6-(benzyloxy)phenyl | H | MS: 429.3 (ES+) |
| 110 | H | 6-methyl-3-oxo-3,4-dihydro-2H-benzo[b][1,4]oxazin-7-yl | H | MS: 350.3 (ES+), 348.3 (ES−) |
| 111 | H | 4-methyl-2-nitro-6-(3,4-dichlorobenzyloxy)phenyl | H | MS: 498.1 et 500.1 (ES+) |
| 112 | H | 4-benzylphenyl | H | MS: 369.4 (ES+) |
| 113 | H | 2-methylnorbornyl | H | MS: 337.4 (ES+), 335.4 (ES−) |
| 114 | H | 4-pyrrolidinophenyl | H | MS: 348.2 (ES+) |

TABLE 5-continued
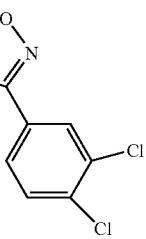
| Example | $R_2$ | $R_7$ | $R_6$ | Characterization data |
|---|---|---|---|---|
| 115 | H | 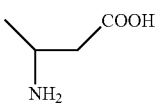 | H | MS: 432.1 (ES+) (+H$_2$O) |
| 116 | H | 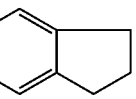 | H | MS: 290.2 (ES+), 288.3 (ES−) |
| 117 | H | 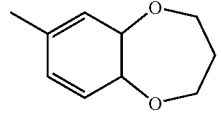 | H | MS: 319.2 (ES+), 317.3 (ES−) |
| 118, HCl | H | 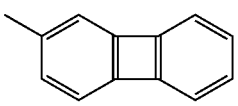 | H | MS: 351.1 (ES+) |
| 119 | H | 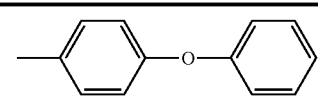 | H | MS: 353.3 (ES+) |
TABLE 6
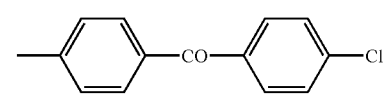
| Example | A | Z | Characterization data |
|---|---|---|---|
| 120 | H | (4-phenoxyphenyl) | m.p. = 198° C.<br>NMR 300 MHz(DMSO): 2.8-2.9(2H, m); 3.0-3.1(1H, m); 3.2-3.3(1H, m); 3.4-3.6(2H, m); 6.8-6.9(1H, m); 6.9-7.2(9H, m); 7.4-7.5(2H, m); 7.5-7.6(2H, m)<br>MS: 387.3 (ES−) |
| 121 | H | (4-(4-chlorobenzoyl)phenyl) | m.p. = 232-233° C.<br>NMR 300 MHz(DMSO): 2.6 (2H, m); 2.8(1H, m); 3.1 (1H, m); 3.2-3.4(2H, m); 6.8-6.9(1H, m); 6.9-7.0(2H, m); 7.0-7.2(1H, m); 7.3-7.4(1H, s); 7.6-7.7(2H, m); 7.7-7.8(6H, m)<br>MS: 435.4 (ES+) |

TABLE 6-continued structure: benzo-fused diazepine with S—CHA—CO—Z substituent at C=N, NH in ring

| Example | A | Z | Characterization data |
|---------|---|---|----------------------|
| 122 | H | 4-trifluoromethylphenyl | MS: 365.2 (ES+) |
| 123 | H | 4-cyanophenyl | MS: 322.2 (ES+) |
| 124 | —C$_6$H$_5$ | —C$_6$H$_5$ | MS: 373.3 (ES+) |
| 125 | —CH$_3$ | —C$_6$H$_5$ | NMR 300 MHz(DMSO): 1.1 (3H, d, J=7.2 Hz); 2.8-3.0 (2H, m); 3.0-3.3(2H, m); 3.9(1H, q, J=7.2 Hz); 6.8-7.2(5H, m); 7.3-7.6(5H, m) MS: 311.3 (ES+) |
| 126 | H | 8-methyl-2-phenyl-4H-chromen-4-one | MS: 440.8 (ES+) |
| 127 | H | methylphenanthrenyl | MS: 394.8 (ES−) |
| 128 | H | methylbenzo[d][1,3]dioxole | MS: 340.7 (ES+) |
| 129 | H | 4-(4-methoxyphenoxy)phenyl | MS: 416.9 (ES−) |
| 130 | H | methyldibenzofuran | MS: 386.8 (ES+) |
| 131 | H | 6-methoxy-2-methylnaphthalene | MS: 376.8 (ES+) |
| 132 | H | 2,3,4-trimethoxyphenyl (methyl) | MS: 387 (ES+) |
| 133 | H | methylfluorene | MS: 385 (ES+) |

TABLE 6-continued

[Structure: benzo-fused 1,3-diazepine with S—CHA—CO—Z substituent on C=N, and NH]

| Example | A | Z | Characterization data |
|---------|---|---|----------------------|
| 134 | H | [4-methyl-2-methoxy-phenyl with O—CH₂—phenyl at position] | MS: 433 (ES+) |
| 135 | H | 4-carboxymethylphenyl | MS: 355 (ES+) |
| 136 | H | [methyl-dibenzofuran-bromo structure] | MS: 465 and 467 (ES+) |
| 137 | H | [2-methyl-5-methyl phenyl with O-allyl] | MS: 367 (ES+) |
| 138 | H | 4-trifluoromesyloxyphenyl | MS: 445 (ES+) |
| 139 | [4-chlorophenyl structure] | —C₆H₅ | MS: 407 (ES+) |
| 140 | H | benzothien-3-yl | MS: 353 (ES+) |
| 141 | H | [phenyl-cyclopentyl-CH₂—NH—SO₂—(4-chlorophenyl)] | MS: 568, 569, 570 and 571 (ES+) |
| 142 | H | [phenyl-cyclobutyl-CH₂—HN—SO₂—(4-chlorophenyl)] | MS: 554, 555, 556 and 557 (ES+); 552, 553, 554 and 555 (ES−) |
| 143 | H | 4-cyanomethylphenyl | MS: 336 (ES+), 334 (ES−) |

TABLE 6-continued

[Structure: benzodiazepine with S—CHA—CO—Z substituent]

| Example | A | Z | Characterization data |
|---------|---|---|------------------------|
| 144 | H | 1-(4-methylbenzyl)-1-cyanocycloheptyl | MS: 432 (ES+) |
| 145 | H | 2-methylphenoxy-CH₂-CO-OCH₃ group | MS: 385 (ES+); 429 (+HCOOH) and 383 (ES−) |
| 146 | H | 4-methylphenyl-CH₂-CO-OCH₃ | MS: 369 (ES+), 367 (ES−) |
| 147 | H | 1-bromo-2-methoxy-6-methylnaphthyl | MS: 455 and 457 (ES+) |
| 148 | H | 4-morpholinophenyl | MS: 382 (ES+) |
| 149 | H | 3,5-bis(acetoxy)-methylphenyl | MS: 413.5 and 454.5 (+CH₃CN) (ES+) |
| 150 | H | 4-benzyloxy-3-methyl-2-methoxy-methylphenyl | MS: 447 (ES+) |
| 151 | H | 4-methylthiophenyl | MS: 343.2 (ES+) |
| 152 | H | 2-chlorothienyl | MS: 337.1 (ES+), 335.1 (ES−) |
| 153 | H | 6-methyltetralinyl | MS: 351.2 (ES+), 349.2 (ES−) |
| 154 | H | 3-(phenylsulfonyl)-methylphenyl | MS: 437.2 (ES+) |
| 155 | H | 2-trifluoromethoxy-phenyl | MS: 381.2 (ES+) |

TABLE 6-continued

Structure: benzodiazepine core with —S—CHA—CO—Z substituent

| Example | A | Z | Characterization data |
|---|---|---|---|
| 156 | H | 4-methylphenyl-O-(4-nitrophenyl) | MS: 434.2 (ES+), 432.2 (ES−) |
| 157 | H | 4-methylphenyl-O-CH₂CH₂-O-CO-CH₃ | MS: 399.3 (ES+), 397.4 (ES−) |
| 158 | H | 4'-methylbiphenyl | MS: 387.4 (ES+), 385.4 (ES−) |
| 159 | H | 3,4-bis(decyloxy)phenyl (O—C₁₀H₂₁) | MS: 609.6 (ES+), 607.6 (ES−) |
| 160 | H | biphenylene | MS: 371.3, 372.3 and 373.3 (ES+); 369.4 (ES−) |
| 161 | H | 3-acetoxy-4-methoxyphenyl | MS: 385.3, 386.4 and 387.4 (ES+); 383.4 (ES−) |
| 162 | H | 2-ethoxy-5-(ethoxycarbonyl)phenyl | MS: 413.4 (ES+), 411.4 (ES−) |
| 163 | H | 2-nitro-3-(phenylthio)phenyl | MS: 450.3 (ES+), 448.4 (ES−) |
| 164 | H | 1,1,4,4,6-pentamethyltetralin | MS: 407.4 (ES+), 405.5 (ES−) |
| 165 | H | bornyl/pinanyl | MS: 355.4 (ES+), 353.4 (ES−) |
| 166 | H | —C(CH₃)₂—CH₂—CO—O—C₂H₅ | MS: 394.4, 350.4 and 351.4 (ES+), 347.4 (ES−) |

TABLE 6-continued

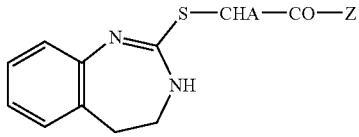

| Example | A | Z | Characterization data |
|---|---|---|---|
| 167 | H | 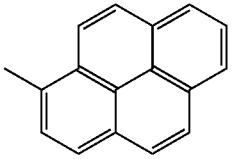 | MS: 421.4 (ES+), 419.4 (ES−) |
| 168 | CH₃ | 4-bromophenyl | MS: 389.3 and 391.3 (ES+); 387.3 and 389.3 (ES−) |
| 169 | H | pentafluoroethyl | MS: 339.3 (ES+), 337.3 (ES−) |
| 170 | H | 4-pyrrolidinophenyl | MS: 366.4 (ES+), 364.4 (ES−) |
| 171 | H | 4-(difluoromethoxy)phenyl | MS: 363.3 (ES+), 361.3 (ES−) |
| 172 | —C₆H₅ | 4-chlorophenyl | MS: 407.3 (ES+), 405.3 (ES−) |
| 173 | 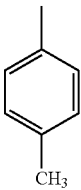 | 4-chlorophenyl | MS: 421.3 (ES+); 419.4 (ES−) |
| 174 | —CH₃ | 3-chloro-4-methylphenyl | MS: 359.3 (ES+), 357.3 (ES−) |
| 175 | H | 3-methylbenzothien-2-yl | MS: 365.3 (ES−) |
| 176 | H | 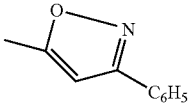 | MS: 364.3 (ES+), 362.3 (ES−) |
| 177 | H | 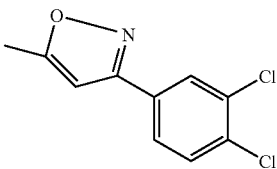 | MS: 433.2 (ES+) |
| 178 | H | 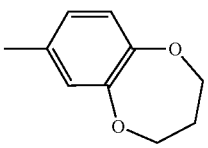 | MS: 369.3 (ES+), 367.4 (ES−) |
| 179 | H | 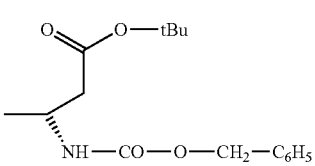 | MS: 498.4 (ES+) |
| 180 | H | 4-cyclohexylphenyl | MS: 379.4 (ES+), 377.4 (ES−) |

TABLE 6-continued

Structure: benzo-fused 1,3-diazepine with S—CHA—CO—Z substituent at C-2 and NH

| Example | A | Z | Characterization data |
|---|---|---|---|
| 181 | H | 4-methyl-2-nitrophenyl ether of 3,4-dichlorobenzyl | NMR 300 MHz(DMSO): 2.8-2.9(2H, m); 3.0-3.4 (2H, m); 3.4-3.6(2H, m); 5.4(2H, s); 6.8-6.9 (1H, m); 6.9-7.0(2H, m); 7.1-7.2(1H, m); 7.4-7.5 (3H, m); 7.6-7.8(3H, m); 8.0-8.1(1H, m) MS: 517.3 (ES+), 514.3 (ES−) |
| 182 | H | 4-trifluoromethylthiophenyl | MS: 397.3 (ES+), 395.3 (ES−) |
| 183 | H | 4-benzylphenyl | MS: 387.4 (ES+), 385.4 (ES−) |
| 184 | —H | 5-chloro-2,3-dimethylbenzothiophenyl | NMR 300 MHz(DMSO): 2.4(3H, s); 2.8-2.9(2H, m); 3.1-3.4(2H, m); 3.4-3.7(2H, m); 6.8-7.2(4H, m); 7.4-7.5(1H, m); 7.7-7.8(2H, m); 7.9-8.0(1H, m) MS: 401.3 (ES+); 399.3 (ES−) |
| 185 | —CH₃ | 4-fluorophenyl | MS: 329.3 (ES+); 327.3 (ES−) |
| 186 | H | 4-(1-ethoxycarbonylcyclopentyl)phenyl | MS: 437.5 (ES+), 435.5 (ES−) |
| 187 | H | 4-(1-acetamidomethylcyclopentylmethyl)phenyl | MS: 450.5 (ES+), 448.5 (ES−) |
| 188 | H | 4-[N-methyl-N-(4-(thiophen-2-yl)butanoyl)amino]phenyl | MS: 478.4 (ES+), 476.4 (ES−) |
| 189 | H | 10-methylanthracenyl | MS: 397.1 (ES+), 395.0 (ES−) |
| 190 | H | 6-methyl-3-oxo-3,4-dihydro-2H-1,4-benzoxazin-yl | MS: 368.2 (ES+), 366.2 (ES−) |

TABLE 6-continued

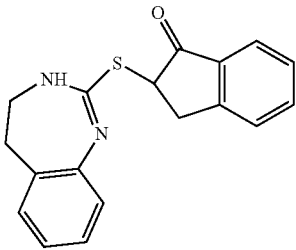

| Example | A | Z | Characterization data |
|---|---|---|---|
| 191 | H | 4-methylcarbonylaminophenyl | MS: 354.2 (ES+), 352.2 (ES−) |

EXAMPLE 192

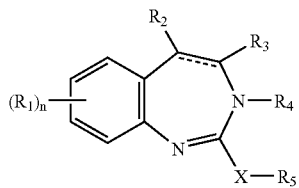

MS: 309.3, 310.3 and 311.3 (ES+), 307.3 (ES−).

The invention claimed is:

1. A benzodiazepine compound of formula I:

![Formula I structure with $R_1$, $R_2$, $R_3$, $R_4$, $R_5$, X, n substituents]

I in which
the dashed lines indicate the possible presence of a double bond;
$R_1$ represents optionally halogenated ($C_1$-$C_{18}$)alkyl, optionally halogenated ($C_1$-$C_{18}$)alkoxy, halogen, nitro, hydroxyl or ($C_6$-$C_{18}$)aryl, which is optionally substituted with optionally halogenated ($C_1$-$C_{10}$)alkyl, optionally halogenated ($C_1$-$C_{12}$)alkoxy, halogen, nitro or hydroxyl;
n represents 0, 1, 2, 3 or 4;
$R_2$ and $R_3$ represent, independently of each other, hydrogen; optionally halogenated ($C_1$-$C_{18}$)alkyl; ($C_1$-$C_{18}$)alkoxy; ($C_6$-$C_{18}$)aryl; ($C_6$-$C_{18}$)aryl($C_1$-$C_{12}$)alkyl; heteroaryl; heteroaryl($C_1$-$C_{12}$)alkyl; ($C_6$-$C_{18}$)aryloxy; ($C_6$-$C_{18}$)aryl($C_1$-$C_{12}$)alkoxy; heteroaryloxy; or heteroaryl($C_1$-$C_{12}$)alkoxy; in which the aryl and heteroaryl portions of these radicals are optionally substituted with halogen, optionally halogenated ($C_1$-$C_{12}$)alkoxy, optionally halogenated ($C_1$-$C_{12}$)alkyl, nitro or hydroxyl;
X represents S;
$R_4$ and $R_5$ together form a group —$CR_6$=$CR_7$— in which $CR_6$ is linked to X;
$R_6$ represents a hydrogen atom; ($C_1$-$C_{18}$)alkyl; ($C_3$-$C_{12}$)cycloalkyl; ($C_6$-$C_{18}$)aryl; carboxy($C_1$-$C_{12}$)alkyl; ($C_1$-$C_{12}$)alkoxycarbonyl($C_1$-$C_{12}$)alkyl; heteroaryl; ($C_6$-$C_{18}$)aryl($C_1$-$C_{12}$)alkyl; or heteroaryl($C_1$-$C_{12}$)alkyl; in which the aryl and heteroaryl portions of these radicals are optionally substituted with ($C_1$-$C_{12}$)alkyl, ($C_1$-$C_{12}$)alkoxy, hydroxyl, nitro, halogen or di($C_1$-$C_{12}$)alkoxyphosphoryl ($C_1$-$C_{12}$)alkyl;
$R_7$ represents a hydrogen atom; hydroxyl; di($C_1$-$C_{12}$)alkylamino($C_1$-$C_{12}$)alkyl; optionally halogenated ($C_1$-$C_{18}$)alkyl; carboxyl; carboxy($C_1$-$C_{12}$)alkyl optionally substituted with amino; ($C_1$-$C_{12}$)alkoxycarbonyl; ($C_6$-$C_{18}$)aryl; heteroaryl; ($C_6$-$C_{18}$)aryl($C_1$-$C_{12}$)alkyl; heteroaryl($C_1$-$C_{12}$)alkyl; ($C_6$-$C_{18}$)aryl fused to an unsaturated heterocycle, optionally substituted on the heterocycle portion with oxo; or ($C_3$-$C_{12}$)cycloalkyl; in which the aryl and heteroaryl portions of these radicals optionally being substituted with ($C_6$-$C_{10}$)aryl, which ($C_6$-$C_{10}$)aryl radical is optionally substituted with halogen, optionally halogenated ($C_1$-$C_6$)alkyl, ($C_1$-$C_6$)alkoxy or nitro; in which the aryl, heterocycle, cycloalkyl and heteroaryl portions of these radicals are optionally substituted with halogen; hydroxyl; hydroxy ($C_1$-$C_{12}$)alkoxy; optionally halogenated ($C_1$-$C_{12}$)alkyl; optionally halogenated ($C_1$-$C_{12}$)alkoxy; carboxyl; ($C_1$-$C_{12}$)alkoxycarbonyl; nitro; cyano; cyano($C_1$-$C_{18}$)alkyl; ($C_1$-$C_{18}$)alkylcarbonyloxy; ($C_2$-$C_{12}$)alkylene; ($C_1$-$C_{12}$)alkylenedioxy; ($C_1$-$C_{12}$)alkylthio; ($C_6$-$C_{18}$)arylthio optionally substituted with one or more substituents Su; di($C_1$-$C_{12}$)alkylamino; a group of formula:

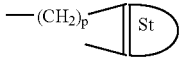

in which p=0, 1, 2, 3 or 4 and in which St represents ($C_6$-$C_{18}$)aryl; -alk-Cy—NH—$SO_2$—Ar in which alk represents ($C_1$-$C_{12}$)alkyl, Cy represents ($C_3$-$C_{12}$)cycloalkyl optionally substituted with one or more substituents Su and Ar represents ($C_6$-$C_{18}$)aryl optionally substituted with one or more substituents Su; —Cy—alk-NH—$SO_2$—Ar; -alk-Cy; -alk-Cy-alk'-NH—CO-alk" in which alk' and alk" represent, independently, ($C_1$-$C_{12}$)alkyl; di($C_1$-$C_{12}$)alkoxyphos-phoryl ($C_1$-$C_{12}$)alkyl; ($C_6$-$C_{18}$)aryl optionally substituted with one or more substituents Su; ($C_6$-$C_{18}$)aryloxy optionally substituted with one or more substituents Su; ($C_6$-$C_{18}$)arylcarbonyl optionally substituted with one or more substituents Su; ($C_6$-$C_{18}$)arylsulphonyl optionally substituted with one or more substituents Su; ($C_6$-$C_{18}$)aryl($C_1$-$C_{12}$)alkoxy in which the aryl portion is optionally substituted with one or more substituents Su; saturated heterocycle optionally substituted with one or more substituents Su; ($C_6$-$C_{18}$)aryl($C_1$-$C_{12}$)alkyl optionally substituted with one or more substituents Su;

Su is hydroxyl, halogen, cyano, nitro, optionally halogenated ($C_1$-$C_{12}$)alkyl or optionally halogenated ($C_1$-$C_{12}$)alkoxy;

or alternatively $R_6$ and $R_7$ together form a $C_3$-$C_{12}$ alkylene chain optionally interrupted with a nitrogen atom which is optionally substituted with ($C_1$-$C_{12}$)alkyl or ($C_6$-$C_{18}$)aryl or ($C_6$-$C_{18}$)aryl($C_1$-$C_{12}$)alkyl, the ring formed by $CR_6$=$CR_7$ optionally being fused to ($C_6$-$C_{18}$)aryl, the aryl portions of these radicals optionally being substituted with halogen, nitro, hydroxyl, optionally halogenated ($C_1$-$C_{12}$)alkyl or optionally halogenated ($C_1$-$C_{12}$)alkoxy;

or a pharmaceutically acceptable salt thereof with an acid or base, wherein the compounds having the following substituents are excluded: X=S; n=0; $R_2$ represents methyl and $R_3$ represents a hydrogen atom; and $R_4$ and $R_5$ together form a group —$CR_6$=$CR_7$— in which $CR_6$ is linked to X, $R_6$ and $R_7$ together form a —$(CH_2)_3$— or —$(CH_2)_4$— chain or alternatively $R_6$ represents a hydrogen atom or a propyl group and $R_7$ is a phenyl group optionally substituted with —$OCH_3$ or a hydroxyl group.

2. A compound according to claim 1, wherein $R_3$ represents a hydrogen atom.

3. A compound according to claim 1, wherein $R_2$ represents a hydrogen atom or a ($C_6$-$C_{10}$)aryl group optionally substituted with halogen, ($C_1$-$C_6$)alkoxy, optionally halogenated ($C_1$-$C_6$)alkyl, nitro or hydroxyl.

4. A compound according to claim 1, wherein n is 0 or 1 and $R_1$ represents a halogen atom.

5. A compound according to claim 1, wherein
$R_6$ represents a hydrogen atom, ($C_1$-$C_6$)alkyl, carboxy($C_1$-$C_6$)alkyl, ($C_1$-$C_6$)alkoxycarbonyl($C_1$-$C_6$)alkyl, or ($C_6$-$C_{10}$)aryl, that is optionally substituted with halogen, hydroxyl, nitro, ($C_1$-$C_6$)alkyl or ($C_1$-$C_6$)alkoxy; and $R_7$ represents a hydrogen atom; hydroxyl; di($C_1$-$C_6$)alkylamino($C_1$-$C_6$)$_5$alkyl; ($C_1$-$C_{10}$)alkyl; ($C_1$-$C_6$)alkoxycarbonyl; ($C_6$-$C_{10}$)aryl; heteroaryl; ($C_6$-$C_{10}$)aryl($C_1$-$C_6$)alkyl; the aryl and heteroaryl portions of these radicals optionally being substituted with ($C_1$-$C_6$)alkoxycarbonyl, halogen, hydroxyl, ($C_1$-$C_6$)alkyl, ($C_6$-$C_{10}$)aryl, which ($C_6$-$C_{10}$)aryl radical is optionally substituted with halogen, optionally halogenated ($C_1$-$C_6$)alkyl, ($C_1$-$C_6$)alkoxy or nitro; or alternatively $R_6$ and $R_7$ together form an alkylene chain interrupted with a nitrogen atom optionally substituted with ($C_6$-$C_{10}$)aryl($C_1$-$C_6$)alkyl in which the aryl portion is optionally substituted with halogen, optionally halogenated ($C_1$-$C_6$)alkyl, ($C_1$-$C_6$)alkoxy, hydroxyl or nitro.

6. A compound, which is
3-(biphenyl-4-yl)-5,6-dihydrothiazolo[2,3-b]-1,3-benzodiazepine;
3-(2-furyl)-5,6-dihydrothiazolo[2,3-b]-1,3-benzodiazepine;
3-[4-(ethoxycarbonyl)phenyl]-5,6-dihydrothiazolo-[2,3-b]-1,3-benzodiazepine;
3-(biphenyl-3-yl)-5,6-dihydrothiazolo[2,3-b]-1,3-benzodiazepine;
3-(3,4-dihydroxyphenyl)-5,6-dihydrothiazolo[2,3-b]-1,3-benzodiazepine; or 3-(biphenyl-4-yl)-7-chloro-5,6-dihydrothiazolo[2,3-b]-1,3-benzodiazepine,
or a pharmaceutically acceptable salt thereof.

7. A process for preparing a compound of formula I according to claim 1, in which X represents S, comprising reacting a thione of formula IIa:

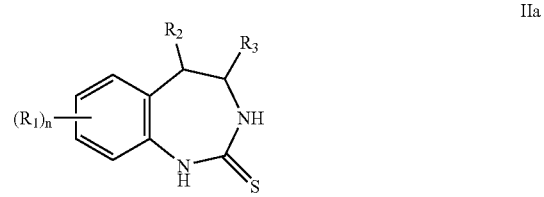

in which n, $R_1$, $R_2$ and $R_3$ are as defined in claim 1, with an α-halo ketone of formula IVb:

in which $R_6$ and $R_7$ are as defined in claim 1, and $Hal^3$ represents a halogen atom,
in a $C_2$-$C_6$ aliphatic carboxylic acid, at a temperature of 90 to 130° C.

8. A process according to claim 7, wherein the aliphatic carboxylic acid is acetic acid.

9. A process according to claim 7, wherein the temperature is maintained at 100 to 125° C.

10. A pharmaceutical composition comprising a compound of formula (I) according to claim 1 and a pharmaceutically acceptable vehicle.

11. A method for treating dyslipidaemia, atherosclerosis or diabetes, comprising administering to a patient in need thereof an effective amount of a compound according to claim 6.

12. A method for treating dyslipidaemia, atherosclerosis or diabetes, comprising administering to a patient in need thereof an effective amount of a compound according to claim 1.

13. A process according to claim 7, wherein the reaction is at a temperature of 60 to 100° C.

14. A compounds which is
3-(biphenyl-4-yl)-5,6-dihydrothiazolo[2,3-b]-1,3-benzodiazepine;
3-(2-furyl)-5,6-dihydrothiazolo[2,3-b]-1,3-benzodiazepine;
3-[4-(ethoxycarbonyl)phenyl]-5,6-dihydrothiazolo-[2,3-b]-1,3-benzodiazepine;
3-(3,4-dihydroxyphenyl)-5,6-dihydrothiazolo[2,3-b]-1,3-benzodiazepine; or
3-(biphenyl-4-yl)-7-chloro-5,6-dihydrothiazolo[2,3-b]-1,3-benzodiazepine.

15. A method for treating dyslipidaemia, atherosclerosis or diabetes, comprising administering to a patient in need thereof an effective amount of a compound according to claim 14.

16. A compound according to claim 5, wherein $R_6$ represents a hydrogen atom, ($C_1$-$C_6$)alkyl, carboxy($C_1$-$C_6$)alkyl, or ($C_1$-$C_6$)alkoxycarbonyl($C_1$-$C_6$)alkyl.

* * * * *

UNITED STATES PATENT AND TRADEMARK OFFICE
CERTIFICATE OF CORRECTION

PATENT NO.        : 7,323,458 B1                                              Page 1 of 1
APPLICATION NO. : 10/019683
DATED             : January 29, 2008
INVENTOR(S)       : Jean-Jacques Berthelon It is certified that error appears in the above-identified patent and that said Letters Patent is hereby corrected as shown below:

Column 68, line 41 reads "compounds" should read -- compound --

Signed and Sealed this

Eighth Day of July, 2008

JON W. DUDAS
*Director of the United States Patent and Trademark Office*